US012616403B2

(12) United States Patent
    Hirai et al.

(10) Patent No.: US 12,616,403 B2
(45) Date of Patent: May 5, 2026

(54) THERMALLY INSULATED CONTAINER AND MAGNETOSPINOGRAPH USING SAME

(71) Applicant: Arisawa MFG. Co., Ltd., Niigata (JP)

(72) Inventors: Masaaki Hirai, Niigata (JP); Toshio Nakamura, Niigata (JP)

(73) Assignee: Arisawa MFG. Co., Ltd. (JP)

( * ) Notice: Subject to any disclaimer, the term of this patent is extended or adjusted under 35 U.S.C. 154(b) by 119 days.

(21) Appl. No.: 18/560,774

(22) PCT Filed: May 19, 2022

(86) PCT No.: PCT/JP2022/020761
    § 371 (c)(1),
    (2) Date: Nov. 14, 2023

(87) PCT Pub. No.: WO2022/249960
    PCT Pub. Date: Dec. 1, 2022

(65) Prior Publication Data
    US 2024/0269959 A1     Aug. 15, 2024

(30) Foreign Application Priority Data
    May 28, 2021     (JP) ................................. 2021-090086

(51) Int. Cl.
    *A61B 5/248*          (2021.01)
    *A61B 5/00*           (2006.01)
    (Continued)

(52) U.S. Cl.
    CPC ................ *A61B 5/248* (2021.01); *A61B 5/70* (2013.01); *B32B 3/12* (2013.01); *B32B 5/024* (2013.01);
    (Continued)

(58) Field of Classification Search
    CPC ...... A61B 5/248; A61B 5/70; G01R 33/0047; G01R 33/0082; G01R 33/0354; F17C 2203/03–0358; F17C 2203/0658–0675
    See application file for complete search history.

(56) References Cited

U.S. PATENT DOCUMENTS

| | | | | | |
|---|---|---|---|---|---|
| 3,317,074 | A | * | 5/1967 | Long | F17C 3/06 428/117 |
| 3,372,075 | A | * | 3/1968 | Holt | F17C 3/02 428/116 |

(Continued)

FOREIGN PATENT DOCUMENTS

| | | |
|---|---|---|
| CN | 109383076 A | 2/2019 |
| CN | 112826511 A | 5/2021 |

(Continued)

OTHER PUBLICATIONS

Machine translation of JPH07302933A (Year: 2025).*

(Continued)

*Primary Examiner* — Christopher R Zerphey
(74) *Attorney, Agent, or Firm* — MASCHOFF BRENNAN

(57)                    ABSTRACT

A thermally insulated container (10) includes an inner container (11), and an outer container (14) surrounding the inner container (11) via a void (15). Each of the inner container (11) and the outer container (14) contains a fiber reinforced plastic prepared by impregnating a base material with a resin. The inner container (11) includes a first tubular container (13) and a second tubular container (22) each having an internal holder (23, 24) to reserve a refrigerant (16), and a refrigerant inlet tube (12) through which the refrigerant (16) is introduced. The holder (24) is in communication with the holder (23). The base material in each of a predetermined area of the second tubular container (22) and a predetermined area of the outer container (14) contains (Continued)

woven fabrics. The predetermined area of the outer container (14) further includes a honeycomb sheet.

18 Claims, 9 Drawing Sheets

(51) Int. Cl.

| | |
|---|---|
| *B23B 3/12* | (2006.01) |
| *B23B 5/02* | (2006.01) |
| *B23B 5/12* | (2006.01) |
| *B23B 5/26* | (2006.01) |
| *B32B 3/12* | (2006.01) |
| *B32B 5/02* | (2006.01) |
| *B32B 5/12* | (2006.01) |
| *B32B 5/26* | (2006.01) |
| *G01R 33/00* | (2006.01) |
| *G01R 33/035* | (2006.01) |

(52) U.S. Cl.
CPC ............... *B32B 5/12* (2013.01); *B32B 5/263* (2021.05); *G01R 33/0047* (2013.01); *G01R 33/0354* (2013.01); *B32B 2250/05* (2013.01); *B32B 2250/40* (2013.01); *B32B 2260/023* (2013.01); *B32B 2260/046* (2013.01); *B32B 2262/10* (2013.01); *B32B 2262/101* (2013.01); *B32B 2262/106* (2013.01); *B32B 2307/302* (2013.01); *B32B 2307/54* (2013.01); *B32B 2307/546* (2013.01); *B32B 2307/7376* (2023.05); *B32B 2439/40* (2013.01)

(56) References Cited

U.S. PATENT DOCUMENTS

| | | | | |
|---|---|---|---|---|
| 3,415,408 | A * | 12/1968 | Seitz | F17C 3/08 |
| | | | | 220/560.12 |
| 4,136,222 | A * | 1/1979 | Jonnes | B32B 3/12 |
| | | | | 428/116 |
| 4,330,494 | A * | 5/1982 | Iwata | E04C 2/205 |
| | | | | 264/46.7 |
| 4,879,152 | A * | 11/1989 | Green | B32B 27/12 |
| | | | | 428/116 |
| 5,065,582 | A * | 11/1991 | Seifert | G01R 33/0354 |
| | | | | 505/879 |
| 5,349,291 | A * | 9/1994 | Kotani | G01R 33/0358 |
| | | | | 505/846 |

| | | | | |
|---|---|---|---|---|
| 6,332,324 | B1 * | 12/2001 | Saho | G01R 33/035 |
| | | | | 62/51.1 |
| 7,130,675 | B2 * | 10/2006 | Ewing | A61B 5/245 |
| | | | | 600/409 |
| 7,296,769 | B2 * | 11/2007 | Hogenson | B64G 1/14 |
| | | | | 244/171.7 |
| 8,383,231 | B2 * | 2/2013 | Horigome | B32B 3/12 |
| | | | | 428/116 |
| 9,027,782 | B1 * | 5/2015 | Shanmugavelayudam | .................. |
| | | | | B32B 5/245 |
| | | | | 220/592.24 |
| 11,852,297 | B2 * | 12/2023 | Mencattelli | F17C 1/06 |
| 2010/0313574 | A1 | 12/2010 | Koyanagi et al. | |
| 2017/0253965 | A1 * | 9/2017 | Takada | C09D 7/61 |
| 2018/0092561 | A1 * | 4/2018 | Kawabata | A61B 5/242 |
| 2019/0059758 | A1 | 2/2019 | Yamaga et al. | |
| 2021/0156931 | A1 | 5/2021 | Yasui | |
| 2024/0175944 | A1 * | 5/2024 | Hirai | G01R 33/007 |

FOREIGN PATENT DOCUMENTS

| | | |
|---|---|---|
| JP | H05-203711 A | 8/1993 |
| JP | H063427 A | 1/1994 |
| JP | H07302933 A | 11/1995 |
| JP | 2002057377 A | 2/2002 |
| JP | 3770026 B2 | 4/2006 |
| JP | 2009-124886 A | 6/2009 |
| JP | 2011023702 A | 2/2011 |
| JP | 2013207018 A | 10/2013 |
| JP | 2017-054924 A | 3/2017 |
| JP | 2018057843 A | 4/2018 |
| WO | 199964796 A1 | 12/1999 |

OTHER PUBLICATIONS

JPH07302933 machine translation (Year: 2025).*

Japan Patent Office; Office Action dated Jan. 14, 2025, issued for the corresponding JP patent application No. 2023-523438 and the English translation.

International Search Report and Written Opinion of the International Searching Authority for International Application No. PCT/JP2022/020761, mailed Aug. 16, 2022. (English translation included).

The Office Action issued by the Taiwan Intellectual Property Office dated Dec. 26, 2011 for the Taiwanese Patent Application No. 11121262480. (Machine English translation included).

Extended European Search Report (EESR) dated Aug. 20, 2024, issued for the corresponding EP patent application No. 22811232.2.

* cited by examiner

10

UP

DOWN

CL

THERMALLY INSULATED CONTAINER AND MAGNETOSPINOGRAPH USING SAME

TECHNICAL FIELD

The present disclosure relates to a thermally insulated container and a magnetospinograph including the thermally insulated container.

BACKGROUND ART

In the medical field, a magnetospinograph, which is an apparatus for measuring magnetic fields generated in response to neural activities in a spinal cord, has been developed. Such a magnetospinograph measures weak magnetic fields generated in the spinal cord with a superconducting quantum interference device (hereinafter referred to as "SQUID") based on the principle of superconducting property.

In order to achieve a superconducting state, the SQUID is required to be immersed in a refrigerant, such as liquid helium. The magnetospinograph thus demands a thermally insulated container having excellent thermal insulation properties and capable of reserving the refrigerant for a long period. This thermally insulated container needs to contain non-magnetic materials unsusceptible to magnetic force.

For example, Patent Literature 1 discloses an extremely low temperature container including an inner container made of a fiber reinforced plastic (hereinafter also referred to as "FRP") and an outer container surrounding the inner container, and discloses a magnetic detecting apparatus including this extremely low temperature container. The inner container is filled with a liquid having a low boiling point. A magnetic detecting sensor is installed in this liquid. The void between the inner container and the outer container is in a vacuum state.

CITATION LIST

Patent Literature

Patent Literature 1: Unexamined Japanese Patent Application Publication No. H7-302933

SUMMARY OF INVENTION

Technical Problem

Since the magnetospinograph measures weak magnetic fields, the distance (lift-off) between the SQUID and the measurement target site of a spinal cord must be made as short as possible. In particular, the thermally insulated container located between the SQUID and the measurement target site of the spinal cord is required to include walls having a reduced thickness, while maintaining sufficient thermal insulation performance.

The inner container and the outer container disclosed in Patent Literature 1 include thick walls in order to improve the thermal insulation performance. Unfortunately, these thick walls inhibit the SQUID from detecting weak magnetic fields.

An objective of the present disclosure, which has been accomplished in view of the above situations, is to provide a thermally insulated container characterized by excellent thermal insulation properties and thin walls, and a magnetospinograph including the thermally insulated container.

Solution to Problem

In order to achieve the above objective, [1] a thermally insulated container according to a first aspect of the present disclosure includes an inner container and an outer container surrounding the inner container via a void. Each of the inner container and the outer container is made of a fiber reinforced plastic prepared by impregnating a base material including fibers with a resin. The inner container includes a first tubular container and a second tubular container each having an internal holder to reserve a refrigerant, and a refrigerant inlet tube through which the refrigerant is introduced into the first tubular container. The holder of the second tubular container is in communication with the holder of the first tubular container. The base material in each of a predetermined area of the second tubular container and a predetermined area of the outer container contains woven fabrics. The predetermined area of the outer container further contains a honeycomb sheet. The woven fabrics are stacked on one and the other surfaces of the honeycomb sheet.

[2] The woven fabrics may contain at least one selected from the group consisting of glass fibers, alumina fibers, and carbon fibers.

[3] The base material in the predetermined area of the outer container may further contain a unidirectional fiber sheet fabricated by aligning multiple fibers to one direction. The unidirectional fiber sheet may be stacked on at least one of the one and the other surfaces of the honeycomb sheet.

[4] The direction of the fibers of the unidirectional fiber sheet in the predetermined area of the outer container may be parallel to the direction of extension of the central axis of the second tubular container.

[5] The base material in the predetermined area of the second tubular container may further contain a unidirectional fiber sheet fabricated by aligning multiple fibers to one direction.

[6] The direction of the fibers of the unidirectional fiber sheet in the predetermined area of the second tubular container may be orthogonal to the direction of extension of the central axis of the second tubular container.

[7] The outer container may surround the second tubular container such that the unidirectional fiber sheet in the predetermined area of the outer container is opposed to the unidirectional fiber sheet in the predetermined area of the second tubular container.

[8] The unidirectional fiber sheet in the predetermined area of the outer container may contain at least one selected from the group consisting of glass fibers, alumina fibers, and carbon fibers.

[9] The unidirectional fiber sheet in the predetermined area of the second tubular container may contain at least one selected from the group consisting of glass fibers, alumina fibers, and carbon fibers.

[10] The honeycomb sheet may have a thickness of 1 to 7 mm.

[11] The resin may contain an epoxy resin.

[12] A magnetospinograph according to a second aspect of the present disclosure includes a superconducting quantum interference device to detect magnetic fields generated from a living body, and the thermally insulated container according to any one of the above-described [1] to [11]. The superconducting quantum interference device is immersed in the refrigerant reserved in the holder of the second tubular container.

Advantageous Effects of Invention

The present disclosure can provide a thermally insulated container characterized by excellent thermal insulation properties and thin walls, and a magnetospinograph including the thermally insulated container.

DESCRIPTION OF EMBODIMENTS

A thermally insulated container and a magnetospinograph including the thermally insulated container according to an embodiment of the present disclosure are described in detail below. The embodiment below is a mere example intended to facilitate an understanding of the present disclosure and is not to be construed as limiting the scope of the present disclosure. The present disclosure can be appropriately modified within the gist of the present disclosure.

Embodiment

Figure 1:
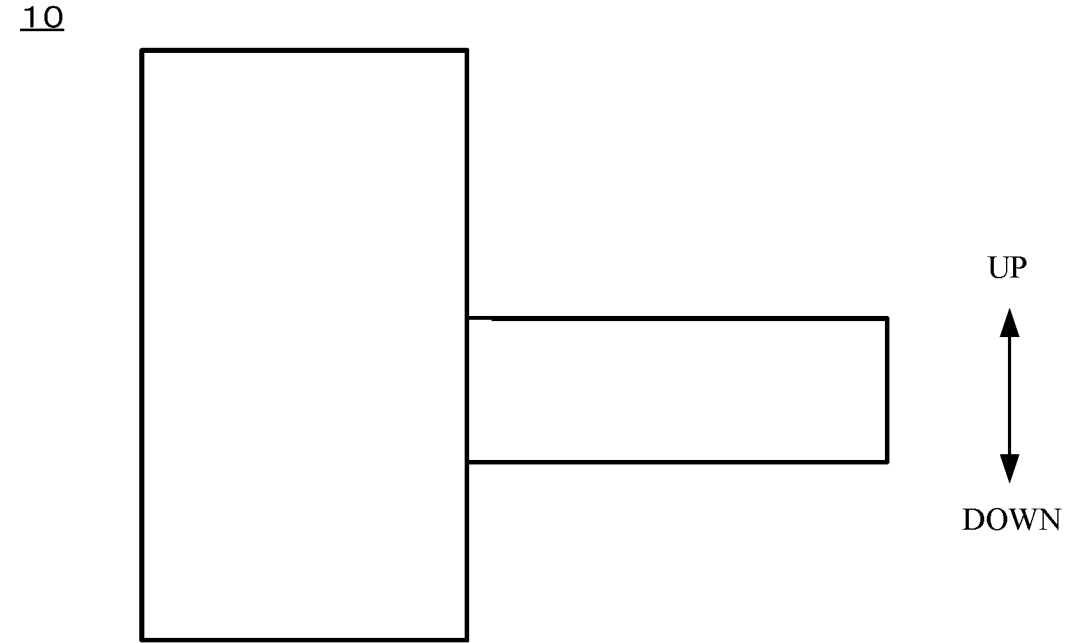
FIG. 1 is a schematic side view of a thermally insulated container according to an embodiment of the present disclosure.
Figure 2:
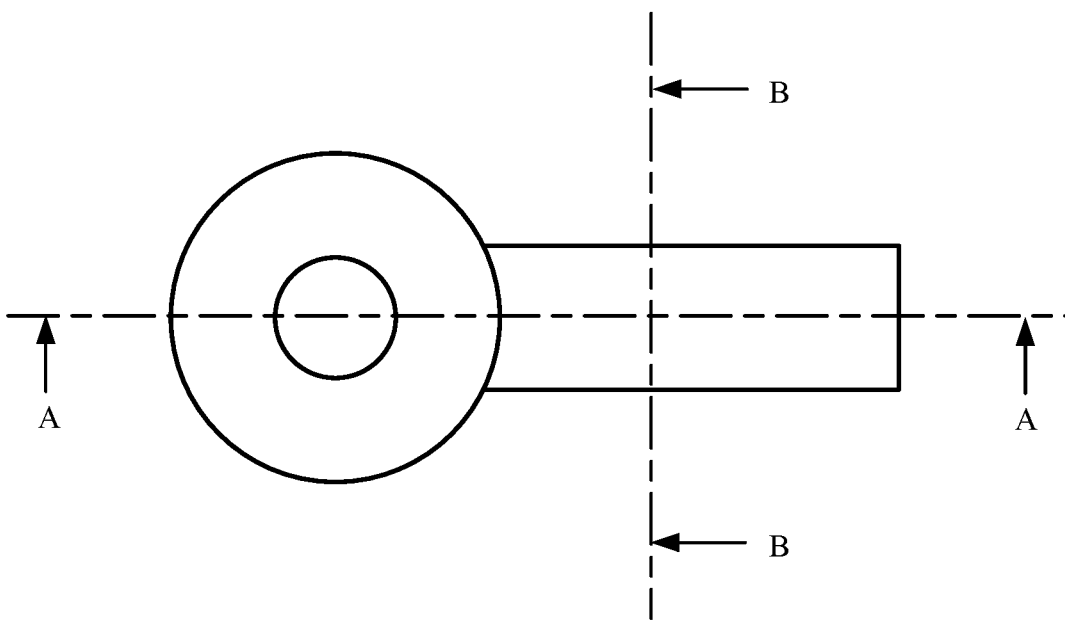
FIG. 2 is a schematic top view of the thermally insulated container according to the embodiment of the present disclosure.
Figure 3:
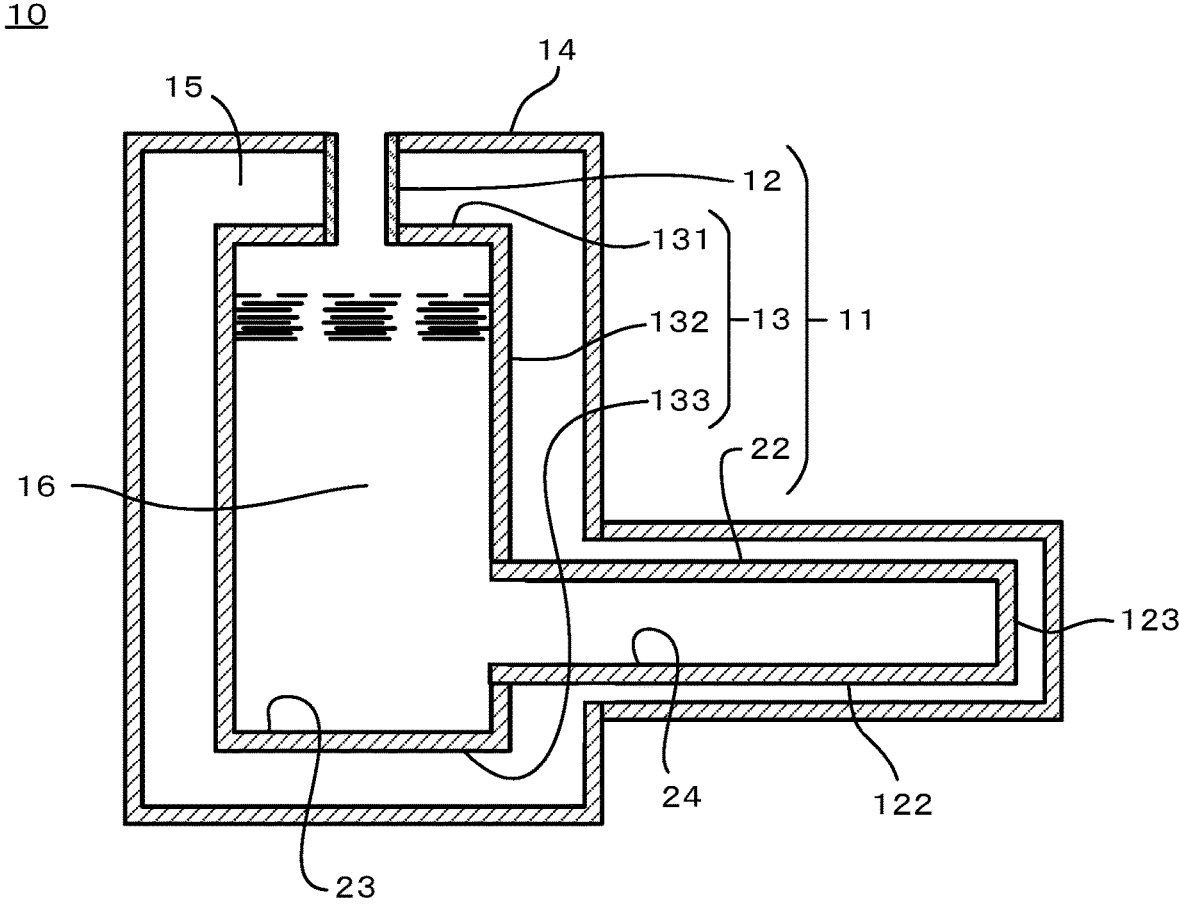
FIG. 3 is a sectional view taken along the line A-A of FIG. 2.

A thermally insulated container 10 according to an embodiment is described below. FIG. 1 is a side view of the thermally insulated container 10. FIG. 2 is a top view of the thermally insulated container 10. FIG. 3 is a sectional view of the thermally insulated container 10 taken along the line A-A of FIG. 2. As illustrated in FIG. 3, the thermally insulated container 10 serves to reserve a refrigerant 16. The thermally insulated container 10 includes an inner container 11, and an outer container 14 surrounding the inner container 11 via a void 15.

The description is first directed to the inner container 11 and the outer container 14.

Inner Container 11

The inner container 11 includes a first tubular container 13 including an internal holder 23 for reserving the refrigerant 16, a refrigerant inlet tube 12 fixed to the first tubular container 13, and a second tubular container 22 including an internal holder 24 for reserving the refrigerant 16. The holder 24 is in communication with the holder 23. The first tubular container 13 includes a ceiling segment 131 constituting the upper surface, a tubular segment 132 constituting the circumferential wall, and a bottom segment 133 constituting the bottom surface. The refrigerant inlet tube 12 is fixed to the ceiling segment 131. Alternatively, the refrigerant inlet tube 12 may be fixed to the tubular segment 132.

The "internal" area in the inner container 11 indicates an area defined by the surfaces that are possibly in contact with the refrigerant 16.

The description is then directed to the refrigerant inlet tube 12, the first tubular container 13, and the second tubular container 22.

Refrigerant Inlet Tube 12

The refrigerant inlet tube 12 is a tubular body through which the refrigerant 16 is introduced into the first tubular container 13. Examples of the shape of the tubular body include a circular cylindrical shape, an elliptic cylindrical shape, and a prism shape.

The wall of the refrigerant inlet tube 12 preferably has a thickness of 2 to 30 mm, and more preferably 2.5 to 15 mm, in terms of improving the thermal insulation properties, and in terms of achieving sufficient rigidity at ordinary temperatures and in the temperature region of at most $-196°$ C. achieved by the refrigerant 16. The "temperature region of at most $-196°$ C." is hereinafter referred to as "extremely low temperature region". The thickness of the wall of the refrigerant inlet tube 12 indicates the thickness of the wall of the refrigerant inlet tube 12 in a plane orthogonal to the longitudinal direction (height direction) of the refrigerant inlet tube 12.

The length of the refrigerant inlet tube 12 is determined depending on the sizes of the outer container 14 and the inner container 11, and is 100 to 500 mm, for example.

In an exemplary case where the refrigerant inlet tube 12 has a circular cylindrical shape, the refrigerant inlet tube 12 has a diameter (inner diameter) of 50 to 300 mm, for example, in terms of reducing evaporation of the refrigerant 16.

In an exemplary case where the refrigerant inlet tube 12 has an elliptic cylindrical shape, the major axis has a length of 50 to 300 mm, for example.

In an exemplary case where the refrigerant inlet tube 12 has a prism shape, the diagonal line has a length of 100 to 400 mm in a section of the tubular body in a plane orthogonal to the longitudinal direction (height direction) of the refrigerant inlet tube 12, for example.

The refrigerant inlet tube 12 is made of a fiber reinforced plastic (hereinafter referred to as "FRP") containing a base material 21 and a resin impregnated in the base material 21.

The resin in the FRP is in the stage after completion of a curing reaction (hereinafter also referred to as "in the C-stage"). In the following description, the state of curing of the FRP is the C-stage, unless otherwise stated. The same holds true for the other embodiments.

The base material 21 of the FRP in the refrigerant inlet tube 12 contains at least one selected from the group consisting of glass fibers, alumina fibers, and carbon fibers. The base material 21 preferably contains glass fibers, in terms of costs, processability, and availability of materials, and in terms of reducing the thermal conductivity in the range of the ordinary temperatures to the extremely low temperature region.

Figure 4:
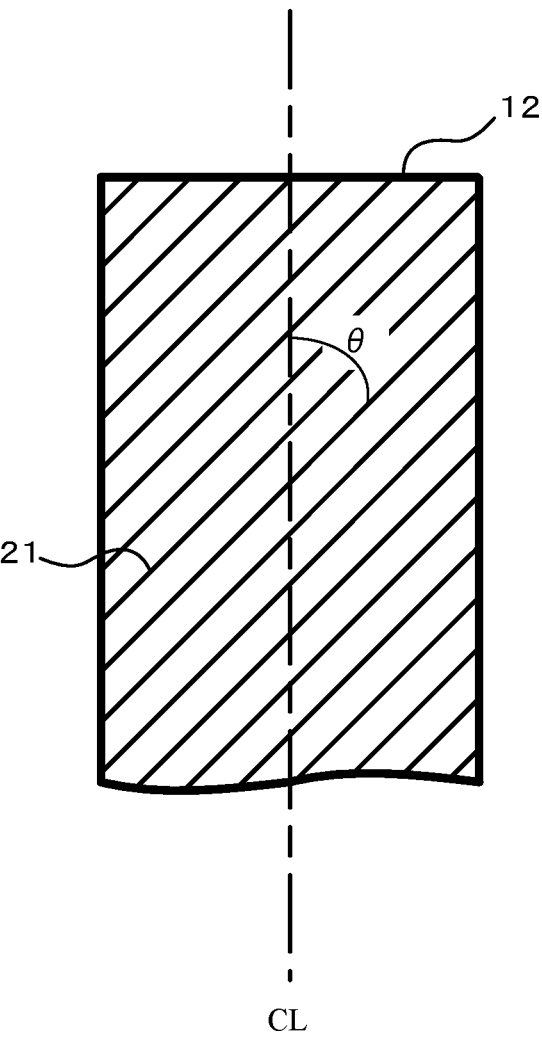
FIG. 4 is a schematic diagram illustrating a structure of a refrigerant inlet tube illustrated in FIG. 3.

As illustrated in FIG. 4, the fibers of the base material 21 are wound in a helix around the direction of extension of the central axis CL of the refrigerant inlet tube 12, in order to delay heat conduction from the outside via the refrigerant inlet tube 12 to the first tubular container 13. The direction of alignment of the fibers forms an angle $\theta$ of $50°$ to $89°$ from the direction of extension of the central axis CL of the refrigerant inlet tube 12. More preferably, the angle $\theta$ is $55°$ to $70°$, in terms of delaying heat conduction in the refrigerant inlet tube 12 and in terms of enhancing the rigidity.

Examples of the resin to be impregnated in the base material 21 include epoxy resin compositions mainly made of an epoxy resin, phenol resin compositions mainly made of a phenol resin, and polyimide resin compositions mainly made of a thermosetting polyimide resin.

An amount of the resin to be impregnated in the base material 21 is preferably 15 to 50 wt % with respect to the total weight of the FRP in the refrigerant inlet tube 12, in terms of delaying heat conduction to the first tubular container 13. A ratio of the resin to be impregnated in the base material is hereinafter referred to as "resin amount (wt %)". The resin amount (wt %) indicates a ratio of the weight of the resin content in the FRP to the total weight of the FRP. The resin amount (wt %) is calculated by the following expression: [resin amount (wt %)]=[weight of resin (wt)×100]/[weight of fibers (wt)+ weight of resin (wt)]. The "weight of resin" indicates a weight of the resin on the solid content basis. The weight of the resin on the solid content basis indicates a weight of resin except for volatile contents, such as solvent.

First Tubular Container 13

The first tubular container 13 has a cylindrical shape having a bottom and defines the internal holder 23 for reserving the refrigerant 16. The holder 23 is defined inside the first tubular container 13. Examples of the shape of the tubular segment 132 of the first tubular container 13 include a circular cylindrical shape, an elliptic cylindrical shape, and a prism shape.

The wall of the first tubular container 13 preferably has a thickness of 2 to 30 mm, and more preferably has a thickness of 2.5 to 15 mm, in terms of improving the thermal insulation properties and in terms of achieving sufficient rigidity in the extremely low temperature region. The thickness of the wall of the first tubular container 13 indicates a thickness of the wall of the tubular segment 132.

In an exemplary case where the first tubular container 13 is applied to an apparatus for measuring magnetic fields in a human body, the first tubular container 13 preferably has a sufficient size to reserve 50 to 150 L of refrigerant in terms of extending the operating period of the apparatus.

Figure 5:
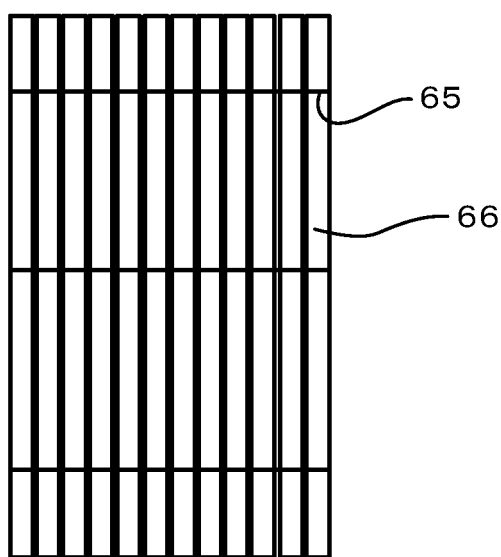
FIG. 5 is a schematic diagram illustrating a structure of a unidirectional fiber sheet.
Figure 6:
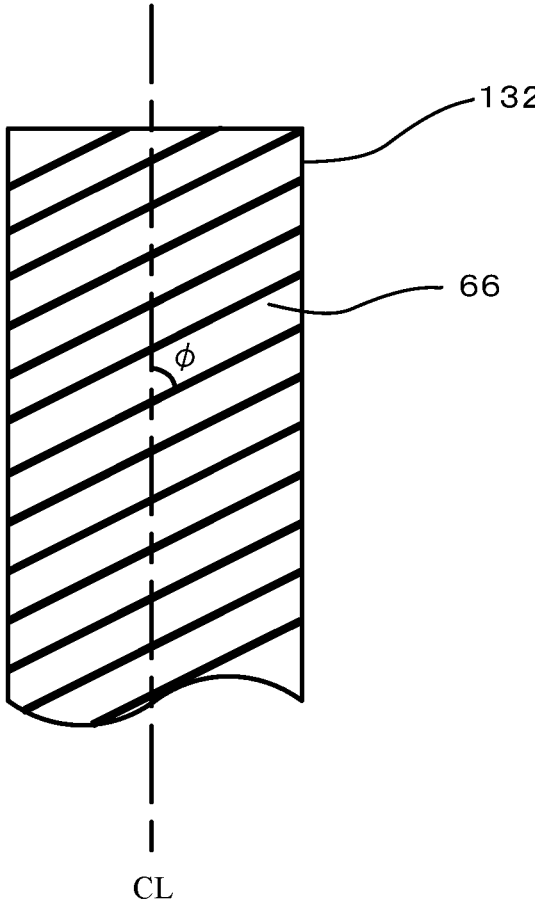
FIG. 6 is a schematic diagram illustrating a structure of a cylindrical segment of a first tubular container illustrated in FIG. 3.

The tubular segment 132 of the first tubular container 13 contains an FRP fabricated by impregnating a base material with a resin. Examples of the base material of the FRP include fibers, woven fabrics, and unidirectional fiber sheets fabricated by aligning multiple fibers to one direction. The base material preferably contains fibers or unidirectional fiber sheets, in order to improve the thermal insulation properties of the first tubular container 13. More preferably, the base material has a structure in which woven fabrics and unidirectional fiber sheets are stacked on each other, in order to improve the rigidity of the tubular segment 132.

i) In the case where the base material contains fibers, the fibers are at least one selected from the group consisting of glass fibers, alumina fibers, and carbon fibers. The fibers are preferably alumina fibers, in terms of reducing thermal conductivity in the extremely low temperature region. The base material may contain a combination of two or more types of fibers, for example, alumina fibers and glass fibers. The fibers are wound in a helix around the direction of extension of the central axis of the tubular segment 132. The angle of the wound fibers is 50° to 89° relative to the direction of extension of the central axis of the tubular segment 132.

ii) In the case where the base material contains woven fabrics, the woven fabrics are fabricated by weaving at least one selected from the group consisting of glass fibers, alumina fibers, and carbon fibers. Examples of the weaving method to fabricate the woven fabrics include sateen, plain, and twill weaves. The woven fabrics are stacked on each other to define a hollow cylindrical shape. For example, the woven fabrics are stacked such that the warps are inclined at +45° and the wefts are inclined at −45° from the direction of extension of the central axis of the tubular segment 132. Alternatively, the woven fabrics may be stacked such that the warps are inclined at 0° and the wefts are inclined at 90° from the direction of extension of the central axis of the tubular segment 132. In terms of achieving quasi-isotropic rigidity, the stacking process may involve first disposing one woven fabric such that the warps are inclined at +45° and the wefts are inclined at −45° from the direction of extension of the central axis of the tubular segment 132, then stacking another woven fabric thereon such that the warps are inclined at 0° and the wefts are inclined at 90°, and repeating these steps, for example. The actual angles of the warps and wefts from the direction of extension of the central axis of the tubular segment 132 do not have to be exactly the same as the above-mentioned predetermined angles and are allowed to be slightly deviated from the predetermined angles provided that sufficient rigidity of the tubular segment 132 is ensured. The allowable range of the angles is +10°, and preferably +5° from the predetermined angles, for example.

iii) In the case where the base material contains unidirectional fiber sheets, each of the unidirectional fiber sheets contains at least one selected from the group consisting of glass fibers, alumina fibers, and carbon fibers. FIG. 5 is a front view of the unidirectional fiber sheets. Each of the unidirectional fiber sheets is fabricated by aligning multiple flat yarns 66 to one direction, as illustrated in FIG. 5. The unidirectional fiber sheet also contains holding yarns 65 that retain the aligned flat yarns 66 and thus prevent the flat yarns 66 from being disarranged, for example. As illustrated in FIG. 6, the unidirectional fiber sheets are wound in a helix and define a hollow cylindrical shape such that the fibers of the flat yarns 66 form an angle q of 50° to 89° from the direction of extension of the central axis CL of the tubular segment 132, for example.

Examples of the resin to be impregnated in the base material in the first tubular container 13 include epoxy resin compositions mainly made of an epoxy resin, phenol resin compositions mainly made of a phenol resin, and polyimide resin compositions mainly made of a thermosetting polyimide resin. The resin is preferably an epoxy resin composition, in terms of ensuring rigidity and toughness of the first tubular container 13 in the range of the ordinary temperatures to the extremely low temperature region, and in terms of ensuring good processability. The resin may also be a mixture of two or more types of resin compositions.

The resin amount of the first tubular container 13 is preferably 15 to 50 wt % with respect to the total weight of the FRP in the first tubular container 13, in terms of maintaining the rigidity of the first tubular container 13 during reservation of the refrigerant 16.

The ceiling segment 131 and the bottom segment 133 of the first tubular container 13 contain an FRP fabricated by impregnating a base material with a resin. The base material contains woven fabrics, for example. The woven fabrics are stacked on each other. The resin is preferably the same as the resin in the tubular segment 132 and the refrigerant inlet tube 12, in terms of making the expansion/contraction behaviors of the tubular segment 132 and the refrigerant inlet tube 12 equal to the expansion/contraction behaviors of the ceiling segment 131 and the bottom segment 133 at the ordinary temperatures and in the extremely low temperature region. The resin amount of the ceiling segment 131 is preferably 15 to 50 wt % with respect to the total weight of the FRP in the ceiling segment 131. The resin amount of the bottom segment 133 is preferably 15 to 50 wt % with respect to the total weight of the FRP in the bottom segment 133. The ceiling segment 131 and the bottom segment 133 have the same thickness as the thickness of the tubular segment 132, for example.

Examples of the refrigerant 16 include liquid oxygen, liquid nitrogen, and liquid helium. The refrigerant 16 is preferably liquid helium for use in measurement of magnetic fields of a spinal cord.

Second Tubular Container 22

The second tubular container 22 includes a tubular segment 122 constituting the side walls, and a bottom segment 123 covering one end of the tubular segment 122. The second tubular container 22 is fixed to the tubular segment 132 of the first tubular container 13. The holder 24 is defined inside the second tubular container 22. The holder 24 is in communication with the holder 23 of the first tubular container 13.

The second tubular container 22 is air-tightly fixed to the tubular segment 132 such that the longitudinal direction of the second tubular container 22 is orthogonal to the longitudinal direction of the tubular segment 132.

Examples of the shape of the second tubular container 22 include a circular cylindrical shape, an elliptic cylindrical shape, and a prism shape. The examples of the prism shape include a shape of column of which a section is a square, trapezoid, or rectangle in a plane orthogonal to the longitudinal direction of the second tubular container 22.

The walls of the tubular segment 122 of the second tubular container 22 may have the same thickness as the thickness of the wall of the first tubular container 13. In an exemplary case where the thermally insulated container 10 is applied to an apparatus for measuring magnetic fields of a spinal cord, the walls of the second tubular container 22 preferably has a thickness of 2 to 15 mm, and more preferably has a thickness of 2.5 to 10 mm, in terms of reducing the lift-off and in terms of improving the thermal insulation properties. The lift-off indicates the distance from the measurement surface of a superconducting quantum interference device to the measurement target site of the spinal cord.

In an exemplary case where the thermally insulated container 10 is applied to an apparatus for measuring magnetic fields of a spinal cord, the second tubular container 22 preferably has a sufficient size to reserve 10 to 30 L of the refrigerant 16 within the second tubular container 22 alone.

The tubular segment 122 is located between a measurement target and the measurement device, and has a predetermined area opposed to the measurement target and the measurement device. The description is first directed to the structure (basic structure) of the areas other than the predetermined area of the tubular segment 122.

The tubular segment 122 has a hollow cylindrical shape and contains an FRP made of a base material and a resin impregnated in the base material. The base material contains i) woven fabrics, ii) unidirectional fiber sheets, or iii) woven fabrics and unidirectional fiber sheets. The base material preferably contains ii) unidirectional fiber sheets or iii) woven fabrics and unidirectional fiber sheets, in terms of avoiding deformation of the tubular segment 122.

i) In the case where the base material contains woven fabrics, the woven fabrics are fabricated by weaving at least one selected from the group consisting of glass fibers, alumina fibers, and carbon fibers. The fibers in the base material are preferably glass fibers or alumina fibers, in terms of maintaining the rigidity of the tubular segment 122 and in terms of ensuring good processability. The fibers in the base material may also be a combination of two or more types of fibers. Examples of the method of weaving to fabricate the woven fabrics include sateen, plain, and twill weaves. The weaving method is preferably a sateen weave in terms of readiness of formation.

The woven fabrics are stacked such that the warps are inclined at 0° and the wefts are inclined at 90° from the direction of extension of the central axis of the tubular segment 122, for example. The woven fabrics may also be stacked such that the warps are inclined at +45° and the wefts are inclined at −45°. In terms of achieving quasi-isotropic rigidity, the stacking process may involve first disposing one woven fabric such that the warps are inclined at 0° and the wefts are inclined at 90° from the direction of extension of the central axis of the tubular segment 122, and then stacking another woven fabric thereon such that the warps are inclined at +45° and the wefts are inclined at −45°.

ii) In the case where the base material contains unidirectional fiber sheets, the unidirectional fiber sheets contain at least one selected from the group consisting of glass fibers, alumina fibers, and carbon fibers. The fibers in the base material are preferably glass fibers or alumina fibers, in terms of maintaining the rigidity of the tubular segment 122 and in terms of ensuring good processability. The base material may contain a combination of two or more types of fibers. The unidirectional fiber sheets are preferably stacked such that the fibers of the unidirectional fiber sheets are arranged to be orthogonal to (inclined at 90° from) the direction of extension of the central axis of the tubular segment 122, in terms of avoiding deformation of the tubular segment 122.

iii) In the case where the base material contains woven fabrics and unidirectional fiber sheets, the base material has a structure in which a woven fabric is stacked on at least one surface of a unidirectional fiber sheet, a structure in which unidirectional fiber sheets are stacked on both surfaces of a woven fabric, or a structure in which woven fabrics and unidirectional fiber sheets are alternately stacked on each other, in terms of avoiding deformation of the tubular segment 122. The woven fabrics and the unidirectional fiber sheets preferably have a structure symmetrical about the woven fabric or the unidirectional fiber sheet located at the center in the thickness direction in a sectional view of the wall of the tubular segment 122, in terms of enhancing the rigidity. For example, the woven fabrics and the unidirectional fiber sheets preferably have a structure in which woven fabrics are stacked on both surfaces of the central unidirectional fiber sheet. This unidirectional fiber sheet is preferably stacked such that the fibers of the unidirectional fiber sheet are arranged to be orthogonal to (inclined at 90° from) the direction of extension of the central axis of the tubular segment 122, in terms of avoiding deformation of the tubular segment 122. The arrangement of the fibers does not have to be exactly orthogonal and is allowed to be slightly inclined provided that sufficient rigidity of the tubular segment 122 is ensured. The allowable range of the angles is 90°±15°, for example.

Figure 8:
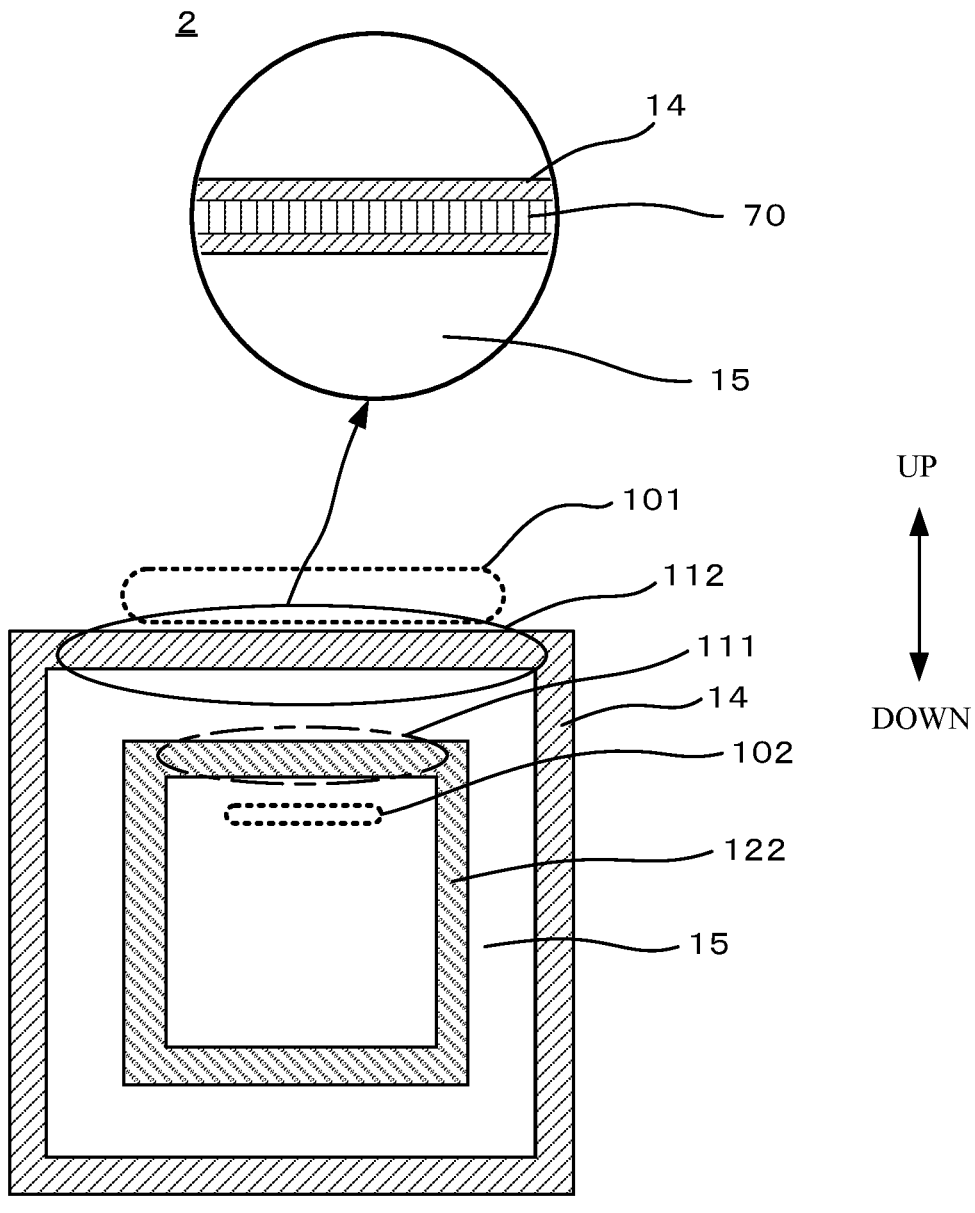
FIG. 8 is a sectional view taken along the line B-B of FIG. 2.

The structure in the predetermined area of the tubular segment 122 is described below focusing on the example illustrated in FIG. 8. FIG. 8 is a sectional view of the thermally insulated container 10 taken along the line B-B of FIG. 2. The "predetermined area" indicates the area to be located between a measurement target 101 and a measurement device 102 during use of the thermally insulated container 10. The predetermined area is required to have a thin wall to reduce the lift-off. The predetermined area of the tubular segment 122 is represented with the reference symbol "111" in FIG. 8. The predetermined area may be a partial area of the upper wall, or the whole area of the upper wall. The "predetermined area" of the outer container 14 is described below.

The predetermined area 111 contains an FRP. The base material of the FRP contains i) woven fabrics or ii) woven fabrics and unidirectional fiber sheets.

i) In the case where the base material contains woven fabrics, the base material in the predetermined area 111 has substantially the same structure as the structure of the areas other than the predetermined area 111 in which the base material contains woven fabrics. That is, the woven fabrics are fabricated by weaving at least one selected from the group consisting of glass fibers, alumina fibers, and carbon fibers. The fibers in the base material are preferably glass fibers or alumina fibers, in terms of maintaining the rigidity of the tubular segment 122 and in terms of ensuring good processability. The base material may also contain two or more types of fibers. Examples of the weaving method to fabricate the woven fabrics include sateen, plain, and twill weaves. The weaving method is preferably a sateen weave, in terms of readiness of formation.

In contrast, ii) in the case where the base material in the predetermined area 111 contains woven fabrics and unidirectional fiber sheets, the base material in the predetermined area 111 has substantially the same structure as the structure of the areas other than the predetermined area 111 in which the base material contains woven fabrics and unidirectional fiber sheets. That is, the base material has a structure in which a woven fabric is stacked on at least one surface of a unidirectional fiber sheet, a structure in which unidirectional fiber sheets are stacked on both surfaces of a woven fabric, or a structure in which woven fabrics and unidirectional fiber sheets are alternately stacked on each other, in terms of avoiding deformation of the tubular segment 122.

In the case where the base material in the predetermined area 111 contains unidirectional fiber sheets, the base material preferably has a structure symmetrical about the woven fabric or the unidirectional fiber sheet located at the center in the thickness direction in a sectional view of the wall of the tubular segment 122, in terms of enhancing the rigidity. For example, the woven fabrics and the unidirectional fiber sheets preferably have a structure in which woven fabrics are stacked on both surfaces of the central unidirectional fiber sheet. This unidirectional fiber sheet is preferably stacked such that the fibers of the unidirectional fiber sheet are arranged to be orthogonal to (inclined at 90° from) the direction of extension of the central axis of the tubular segment 122, in terms of avoiding deformation of the tubular segment 122. The arrangement of the fibers does not have to be exactly orthogonal and is allowed to be slightly inclined provided that sufficient rigidity of the tubular segment 122 is ensured. The allowable range of the angles is 90°+15°, for example.

The base material in the predetermined area 111 containing unidirectional fiber sheets enables the FRP to have high rigidity because the unidirectional fiber sheets provide high rigidity against stresses. This structure can thus achieve a relatively thinner wall while ensuring high rigidity, in comparison to a structure in which the base material contains woven fabrics alone. The structure can therefore allow the measurement device 102 to be located closer to the measurement target 101 during use of the thermally insulated container 10, for example. The predetermined area 111 is preferably the whole area of the upper wall of the tubular segment 122, in terms of maintaining the rigidity.

In an exemplary case where the tubular segment 122 has a circular cylindrical shape, the predetermined area 111 of the tubular segment 122 corresponds to a partial area of the peripheral surface (curved surface) of the semicylinder constituting the half of the circular cylindrical shape, or the whole area of the peripheral surface (curved surface) of the semicylinder.

The resin amount in the predetermined area 111 of the tubular segment 122 and the areas other than the predetermined area 111 is 15 to 50 wt % with respect to the total weight of the FRP in the tubular segment 122, in terms of maintaining the rigidity.

Examples of the resin to be impregnated in the base material in the tubular segment 122 include epoxy resin compositions mainly made of an epoxy resin, phenol resin compositions mainly made of a phenol resin, and polyimide resin compositions mainly made of a thermosetting polyimide resin. The resin is preferably an epoxy resin composition, in terms of ensuring rigidity and toughness at the ordinary temperatures and in the extremely low temperature region, and in terms of ensuring good processability. The resin may be a mixture of two or more types of resin compositions.

The bottom segment 123 contains an FRP made of a base material and a resin impregnated in the base material. The base material contains a stack of multiple woven fabrics. The resin is preferably the same as the resin in the tubular segment 122, in terms of making the expansion/contraction behavior of the tubular segment 122 equal to the expansion/contraction behavior of the bottom segment 123 in the range of the ordinary temperatures to the extremely low temperature region. The resin amount of the bottom segment 123 is preferably 15 to 50 wt % with respect to the total weight of the FRP in the bottom segment 123, like the resin amount of the tubular segment 122, in terms of maintaining the rigidity of the first tubular container 13 during reservation of the refrigerant.

The holder 23 of the first tubular container 13 may be fixed to the holder 24 of the second tubular container 22 such that the holder 23 is in communication with the holder 24 via a member, such as tube. In this case, the member for communication between the holder 23 and the holder 24 is preferably made of the same material as the material of the first tubular container 13 and the second tubular container 22.

Examples of the joining method between the first tubular container 13 and the second tubular container 22 include a method of applying an adhesive to the joint surface of the first tubular container 13 and the joint surface of the second tubular container 22 and thereby air-tightly bonding the joint surfaces to each other, and a method of providing threads to the joint surface of the first tubular container 13 and the joint surface of the second tubular container 22, applying an adhesive to these threads, and then air-tightly screwing the threads together. The joining method can preferably achieve air-tight bonding and maintain the void 15 in a vacuum state.

The applied adhesive is preferably the same as the resin in the refrigerant inlet tube 12 and the first tubular container 13, in terms of ensuring good adhesion properties. Examples of the resin include epoxy resin compositions mainly made of an epoxy resin, phenol resin compositions mainly made of a phenol resin, and polyimide resin compositions mainly made of a thermosetting polyimide resin. The resin is preferably an epoxy resin composition, in terms of ensuring rigidity and toughness in the range of the ordinary temperatures to the extremely low temperature region, and in terms of ensuring good adhesion properties. The resin may be a mixture of two or more types of resin compositions.

Outer Container 14

As illustrated in FIG. 3, the outer container 14 surrounds the inner container 11 via the void 15. The ceiling segment of the outer container 14 supports the first tubular container 13 via the refrigerant inlet tube 12. In the thermally insulated container 10, the end face of the refrigerant inlet tube 12 is flush with the surface of the ceiling segment of the outer container 14.

The state of "surrounding" indicates that the outer container 14 is disposed around the inner container 11 via the void 15 in an encompassing manner. The "internal" area in the outer container 14 indicates an area of the outer container 14 in contact with the void 15. The portion of the outer container 14 constituting the upper surface is referred to as "ceiling segment".

The void 15 is preferably in a vacuum state in terms of improving the heat insulation performance. The outer container 14 has sufficient rigidity to maintain the shape of the outer container 14 despite of the vacuum state of the void 15.

The outer container 14 has any shape and any size provided that the outer container 14 can surround the inner container 11. The outer container 14 preferably has a rounded shape capable of distributing stresses, in terms of avoiding deformation of the container when the void 15 is evacuated. In particular, the corners of the outer container 14 preferably have a shape having a large radius of curvature. This structure can prevent contraction stresses caused by evacuation from being focused on a specific site of the container.

The outer container 14 is also described below with respect to a predetermined area 112 to be located between the measurement target 101 and the measurement device 102 illustrated in FIG. 8 and the areas other than the predetermined area 112, separately. The description is first directed to the structure of the areas other than the predetermined area 112.

The walls of the outer container 14 preferably have a thickness equal to or larger than the thickness of the first tubular container 13 and the second tubular container 22, in terms of preventing the container from being deformed when the void 15 is evacuated.

The areas other than the predetermined area 112 of the outer container 14 contain an FRP made of a base material and a resin impregnated in the base material. The base material in the predetermined area 112 of the outer container 14 may contain i) woven fabrics or ii) woven fabrics and unidirectional fiber sheets.

In the case where the base material contains woven fabrics, the woven fabrics are fabricated by weaving at least one selected from the group consisting of glass fibers, alumina fibers, and carbon fibers. The fibers of the woven fabrics are preferably glass fibers and alumina fibers, in terms of maintaining the rigidity and in terms of ensuring good processability. The base material may also contain a combination of two or more types of fibers. Examples of the weaving method to fabricate the woven fabrics include sateen, plain, and twill weaves. The weaving method is preferably a sateen weave, in terms of ease of shaping.

The woven fabrics may be stacked such that the warps of the woven fabrics are inclined at 0° and the wefts are inclined at 90° from the direction of extension of the central axis of the second tubular container 22, or such that the warps are inclined at +45° and the wefts are inclined at −45°, for example. In terms of achieving quasi-isotropic rigidity, the stacking process may involve first disposing one woven fabric such that the warps are inclined at 0° and the wefts are inclined at 90° from the direction of extension of the central axis of the second tubular container 22, and then stacking another woven fabric thereon such that the warps are inclined at +45° and the wefts are inclined at −45°. The allowable range of the angles of the warps and wefts from the direction of extension of the central axis of the second tubular container 22 is +10°, and preferably +5°.

Examples of the resin in the areas other than the predetermined area 112 of the outer container 14 include epoxy resin compositions mainly made of an epoxy resin, phenol resin compositions mainly made of a phenol resin, and polyimide resin compositions mainly made of a thermosetting polyimide resin. The resin is preferably an epoxy resin composition, in terms of ensuring rigidity and toughness in the range of the ordinary temperatures to the extremely low temperature region, and in terms of ensuring good processability. The resin may be a mixture of two or more types of resin compositions.

The structure of the predetermined area 112 of the outer container 14 is then described with reference to the circle 2 of FIG. 8. The predetermined area 112 of the outer container 14 also contains an FRP. The base material in the predetermined area 112 of the outer container 14 contains i) woven fabrics or ii) woven fabrics and unidirectional fiber sheets.

i) In the case where the base material contains woven fabrics, the base material has the same structure as the base material in the other areas of the outer container 14. That is, the woven fabrics are fabricated by weaving at least one selected from the group consisting of glass fibers, alumina fibers, and carbon fibers. The fibers of the woven fabrics are preferably glass fibers and alumina fibers, in terms of maintaining the rigidity and in terms of ensuring good processability. The base material may also contain two or more types of fibers. Examples of the weaving method to fabricate the woven fabrics include sateen, plain, and twill weaves. The weaving method is preferably a sateen weave, in terms of readiness of formation.

ii) In the case where the base material contains woven fabrics and unidirectional fiber sheets, the woven fabrics are substantially the same as the woven fabrics in the base material in the other areas of the outer container 14. The unidirectional fiber sheets contain at least one selected from the group consisting of glass fibers, alumina fibers, and carbon fibers. The fibers in the base material are preferably glass fibers or alumina fibers, in terms of maintaining the rigidity and in terms of ensuring good processability. The fibers may also be a combination of two or more types of fibers.

The unidirectional fiber sheets are preferably stacked such that the fibers of the unidirectional fiber sheets are parallel to (inclined at 0° from) the direction of extension of the central axis of the second tubular container 22 (tubular segment 122), in terms of enhancing the rigidity and in terms of avoiding deformation of the outer container 14. The parallel (inclined at 0°) arrangement may be slightly inclined provided that sufficient rigidity of the outer container 14 is ensured. The allowable range of the angles is ±10°, and preferably ±5°.

The predetermined area 112 of the outer container 14 is expected to receive the load of the measurement target 101 and is required to have higher rigidity than those in the other areas. In order to meet this requirement, as illustrated in the enlarged view in the circle 2 of FIG. 8, the outer container 14 further includes a honeycomb sheet 70 in the FRP in the predetermined area 112. The honeycomb sheet 70 is resistant to shear force and contributes to thermal insulation properties. Examples of the honeycomb sheet 70 include aramid honeycomb sheets, paper honeycomb sheets, and non-burnable honeycomb sheets. The honeycomb sheet 70 is preferably an aramid honeycomb sheet, in terms of ensuring rigidity. The honeycomb sheet 70 is made of polygonal cells, such as hexagonal cells. One side of each of the hexagonal cells has a length of 3 to 10 mm, and preferably has a length of 3 to 5 mm in terms of maintaining the thermal insulation properties and in terms of retaining the honeycomb shape. The thickness (height) of the honeycomb sheet 70 is 1 to 7 mm, and preferably 1 to 3 mm in terms of maintaining the thermal insulation properties and reducing the thickness of the wall of the outer container 14. Each of the cells has a void space therein for improving the thermal insulation properties. The void space in the cell may be in the vacuum state or be filled with air.

In the case where the base material in the predetermined area 112 contains woven fabrics, the woven fabrics are stacked on both surfaces of the honeycomb sheet 70. In contrast, in the case where the base material in the predetermined area 112 contains woven fabrics and unidirectional fiber sheets, the unidirectional fiber sheet is preferably stacked on at least one of both surfaces of the honeycomb sheet 70. For example, the FRP in the predetermined area 112 of the outer container 14 has i) a structure in which woven fabrics are stacked on both surfaces of the honeycomb sheet 70 and a unidirectional fiber sheet is stacked on at least one of the woven fabrics, ii) a structure in which unidirectional fiber sheets are stacked on both surfaces of the honeycomb sheet 70 and woven fabrics are stacked on the respective unidirectional fiber sheets, or iii) a structure in which a unidirectional fiber sheet is stacked on one surface of the honeycomb sheet 70, a woven fabric is stacked on this unidirectional fiber sheet, and another woven fabric is stacked on the other surface of the honeycomb sheet 70.

The predetermined area 112 of the outer container 14, of which the base material contains both of woven fabrics and unidirectional fiber sheets, has higher rigidity than that of a predetermined area 112 of which the base material contains woven fabrics alone. This structure can achieve a reduced thickness of the wall of the predetermined area 112 of the outer container 14. In addition, the structure containing both of woven fabrics and unidirectional fiber sheets less readily causes deformation of the predetermined area 112 of the outer container 14 despite of a thin wall, in comparison to the structure containing woven fabrics alone.

The predetermined area 112 of the outer container 14 is preferably larger (broader) than the predetermined area 111 of the second tubular container 22, in terms of enhancing the thermal insulation properties and the rigidity.

The resin in the predetermined area 112 of the outer container 14 is preferably the same as the resin in the areas other than the predetermined area 112. That is, examples of the resin include epoxy resin compositions mainly made of an epoxy resin, phenol resin compositions mainly made of a phenol resin, and polyimide resin compositions mainly made of a thermosetting polyimide resin. The resin is preferably an epoxy resin composition, in terms of ensuring rigidity and toughness in the range of the ordinary temperatures to the extremely low temperature region, and in terms of ensuring good processability. The resin may also be a mixture of two or more types of resin compositions.

Alternatively, the base material of the FRP in the areas other than the predetermined area 112 of the outer container 14 may contain woven fabrics and unidirectional fiber sheets. In this case, the woven fabrics and the unidirectional fiber sheets may have a structure in which a woven fabric is stacked on at least one surface of a unidirectional fiber sheet, a structure in which unidirectional fiber sheets are stacked on both surfaces of a woven fabric, or a structure in which woven fabrics and unidirectional fiber sheets are alternately stacked on each other, in terms of avoiding deformation of the outer container 14.

The resin amount of the predetermined area 112 of the outer container 14 is preferably 15 to 50 wt % with respect to the total weight of the FRP in the outer container 14, in terms of maintaining the rigidity of the outer container 14 during reservation of the refrigerant 16.

The void 15 may be provided with supporting members (not illustrated) to support loads and stabilize the first tubular container 13 and the second tubular container 22 at certain positions.

The outer container 14 and the refrigerant inlet tube 12 are air-tightly bonded to each other. Examples of the joining method between the outer container 14 and the refrigerant inlet tube 12 include a method of applying an adhesive to the joint surface of the outer container 14 and the joint surface of the refrigerant inlet tube 12 and thereby air-tightly bonding the joint surfaces to each other, and a method of providing threads to the joint surface of the outer container 14 and the joint surface of the refrigerant inlet tube 12, applying an adhesive to these threads, and then air-tightly screwing the threads together.

Figure 7:
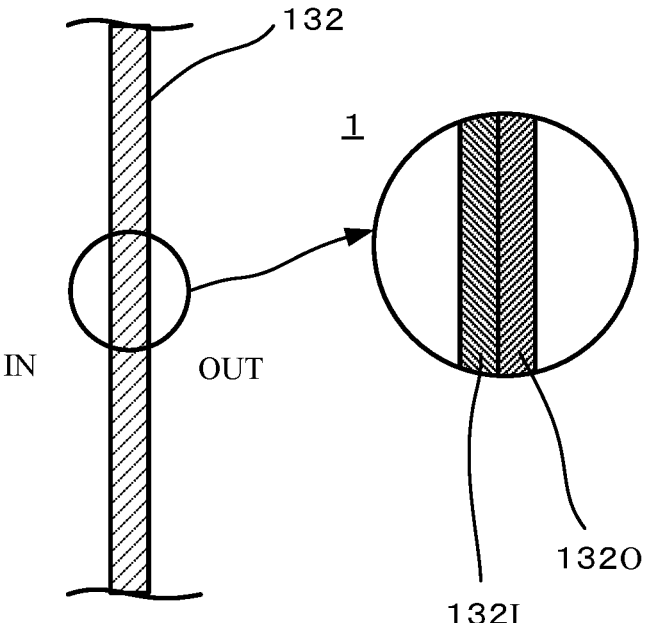
FIG. 7 is a schematic sectional view of a modified structure of the tubular segment of the first tubular container illustrated in FIG. 3.

Although the tubular segment 132 has a single-layer wall in the above-described embodiment, the tubular segment 132 may also have a multi-layer wall. The refrigerant inlet tube 12 and other components having a similar cylindrical shape may also have multi-layer walls. For example, as illustrated in the circle 1 of FIG. 7, the tubular segment 132 may have an outer layer 132O and an inner layer 132I. The outer layer 132O is located closer to the void 15 (outside), while the inner layer 132I is located closer to the refrigerant 16 (inside).

The outer layer 132O and the inner layer 132I each contain an FRP. The base material of the FRP contains fibers or unidirectional fiber sheets. The base material is made of glass or alumina.

The base material in the outer layer 132O preferably contains fibers or unidirectional fiber sheets, in terms of ensuring the rigidity of the tubular segment 132, in terms of reducing the thermal conductivity of the tubular segment 132, and in terms of reducing costs. This base material is preferably made of glass. In contrast, the base material in the inner layer 132I preferably contains fibers or unidirectional fiber sheets. This base material is preferably made of alumina.

The base materials in the outer layer 132O and the inner layer 132I are each wound in a helix around the direction of extension of the central axis of the tubular segment 132. The angles of the fibers or the fibers of the unidirectional fiber sheets from the direction of extension of the central axis of the tubular segment 132 may be different or identical between the outer layer 132O and the inner layer 132I. The angle of the fibers or the fibers of the unidirectional fiber sheets in the inner layer 132I is preferably larger than the angle of the fibers or the fibers of the unidirectional fiber sheets in the outer layer 132O, in terms of enhancing the rigidity of the tubular segment 132, and in terms of improving the workability (readiness of extraction from a mold). The inner layer 132I preferably has the same thickness as the outer layer 132O, or a thickness larger than the outer layer 132O. The ratio of the thickness of the inner layer 132I to the thickness of the outer layer 132O is 50:50 to 80:20, preferably 50:50 to 70:30, and more preferably 50:50 to 60:40.

The resin to be impregnated in the base material in the outer layer 132O is preferably the same as that in the inner layer 132I, in terms of avoiding separation of the layers.

In the case where the FRP in the tubular segment 132 has a double-layer structure, the FRP in the ceiling segment 131 and the bottom segment 133 preferably also has a double-layer structure. The fibers in the outer layers of the ceiling segment 131 and the bottom segment 133 are glass fibers, and the fibers in the inner layers are alumina fibers, for example, in terms of delaying heat conduction from the outside via the refrigerant inlet tube 12 to the entire inner container 11. The resin in the ceiling segment 131 and the bottom segment 133 is preferably the same as the resin in the tubular segment 132.

The following description is directed to methods of fabricating the refrigerant inlet tube 12, the first tubular container 13, the second tubular container 22, and the outer container 14.

Method of Fabricating the Refrigerant Inlet Tube 12

The method of fabricating the refrigerant inlet tube 12 involves a forming step of winding fibers impregnated with a liquid resin, that is, a base material around a rod mold in a helix and thus forming the shape of the refrigerant inlet tube 12, a curing step of heating and curing the resin, and a demolding step of extracting the cured refrigerant inlet tube 12 from the mold.

In the forming step, a typical example of the forming method is a filament winding method. The angle of the fibers wound around the mold is 50° to 89° from the direction of extension of the central axis of the mold.

In the curing step, the temperature and the period for curing of the resin can be appropriately determined depending on conditions, such as a type and an amount of the resin. In an exemplary case where the applied resin is an epoxy resin composition and the resin amount is 20 to 50 wt %, the heating temperature is determined to be 80° C. to 150° C. and the curing period is determined to be 1 to 12 hours.

In the demolding step, the refrigerant inlet tube 12 is allowed to cool to room temperature and then extracted from the mold. This process can yield the refrigerant inlet tube 12.

Method of Fabricating the First Tubular Container 13

The description is then directed to an exemplary method of fabricating the first tubular container 13. The tubular segment 132 of the first tubular container 13 can be fabricated by winding prepregs made of a base material containing fibers, woven fabrics, or unidirectional fiber sheets impregnated with a resin around a rod mold while adjusting the direction of the fibers, curing the prepregs, and then cutting the resultant into a predetermined shape. The ceiling segment 131 and the bottom segment 133 of the first tubular container 13 can each be fabricated by stacking prepregs, curing the prepregs, and cutting the resultant into a predetermined size. The prepreg indicates a composite material of which a resin is cured in the B-stage, that is, the curing reaction of the resin has been advanced but not completed.

The fabricated ceiling segment 131 and the tubular segment 132 are then air-tightly bonded to each other. Examples of the joining method include, bonding the joint surface of the ceiling segment 131 to the tubular segment 132 with an adhesive, and providing threads to the joint surface of the ceiling segment 131 and the joint surface of the tubular segment 132 and then screwing the threads together. The threads may be screwed together after being provided with an adhesive curable at ordinary temperature, for example. This step can air-tightly seal the joint surfaces. This joining method between the ceiling segment 131 and the tubular segment 132 can also be applied to the bonding between the bottom segment 133 and the tubular segment 132. This process can complete the first tubular container 13.

The description is then directed to another example of the method of fabricating the first tubular container 13. This method involves a prepreg fabricating step of impregnating a base material with a resin, heating the base material, and thus fabricating prepregs, a forming step of attaching prepregs on the surface of a mold for defining the shape of the first tubular container 13 and thus forming the shape of the prepregs, a curing step of curing the formed prepregs by heat and pressure, and a demolding step of extracting the cured prepregs from the mold.

In the prepreg fabricating step, the period of impregnation of the base material with the resin and the temperature of heating the woven fabrics after impregnation can be appropriately determined depending on conditions, such as a type of the resin and an amount of the resin (resin amount) adhering to the woven fabrics. In an exemplary case where the applied resin is an epoxy resin composition and the resin amount is 20 to 50 wt %, the period is determined to be 1 to 12 hours and the temperature is determined to be 80° C. to 150° C.

In the forming step, the fabricated prepregs are cut along the shape of the first tubular container 13. The prepregs are attached on the mold to form the shape. In the case where the mold has a complicated shape, the prepregs are cut into small segments and then attached on the mold to form the shape. This process can allow the prepregs to follow the complicated shape.

In the curing step, the formed prepregs are cured by heat and pressure. A typical example of the method of curing the prepregs is an autoclave molding method using a high-pressure furnace. This step can achieve uniform curing of the prepregs.

In the demolding step, the cured prepregs are allowed to cool to room temperature, and then extracted from the mold. This process can yield the first tubular container 13.

In an exemplary case where the tubular segment 132 is made of an FRP and has a double-layer wall, the tubular segment 132 can be fabricated by a filament winding method, for example.

In an exemplary case where the base material in the inner layer contains alumina fibers and the base material in the outer layer contains glass fibers, the tubular segment 132 is fabricated as follows. First, alumina fibers impregnated with a resin are wound in a helix around a rod mold. Then, glass fibers impregnated with a resin are wound in a helix over the wounded alumina fibers, thereby forming the shape of the tubular segment 132 having a double-layer wall. The resultant is then heated to cure the resin in the tubular segment 132. The tubular segment 132 is then allowed to cool to room temperature and extracted from the mold, thereby providing the tubular segment 132 having a double-layer wall.

The ceiling segment 131 and the bottom segment 133 are also fabricated so as to have double-layer walls. The method of fabricating the ceiling segment 131 involves a prepreg fabricating step of fabricating prepregs containing woven fabrics fabricated by weaving alumina fibers as a base material and prepregs containing woven fabrics fabricated by weaving glass fibers as a base material, a stacking step of stacking these two types of prepregs such that the wall has a double layer, and a curing step of curing the stacked prepregs. The bottom segment 133 is fabricated by the same method as the method of fabricating the ceiling segment 131.

The joining method between the ceiling segment 131 and the tubular segment 132 can also be applied to the bonding between the ceiling segment 131 and the tubular segment 132 having double-layer walls, and the bonding between the bottom segment 133 and the tubular segment 132 having double-layer walls.

Method of Fabricating the Second Tubular Container 22

In the method of fabricating the second tubular container 22, the tubular segment 122 and the bottom segment 123 of the second tubular container 22 are prepared separately.

The description is first directed to a method of fabricating the tubular segment 122 containing woven fabrics as a base material. The method of fabricating the tubular segment 122 involves a cloth prepreg fabricating step of fabricating cloth prepregs containing woven fabrics as a base material, a cloth prepreg forming step of attaching cloth prepregs on the surface of a mold for defining the shape of the tubular segment 122 such that the direction of the warps or wefts is orthogonal to the direction of extension of the central axis of the mold and thus forming the shape of the cloth prepregs, a curing step of curing the stacked cloth prepregs, and a demolding step of extracting the cured cloth prepregs from the mold.

In the cloth prepreg fabricating step, woven fabrics are impregnated with a resin. The woven fabrics are then heated. The heating period and the heating temperature can be appropriately determined depending on conditions, such as a type of the resin and an amount of the resin (resin amount) adhering to the woven fabrics. In an exemplary case where the applied resin is an epoxy resin composition and the resin amount is 20 to 50 wt %, the heating period is determined to be 1 to 12 hours and the heating temperature is determined to be 80° C. to 150° C.

In the cloth prepreg forming step, the cloth prepregs are cut in accordance with the size of the mold. The cut cloth prepregs are attached on the mold to form the shape. The cloth prepregs are attached to form the shape such that the direction of the warps or wefts of the woven fabrics is orthogonal to the direction of extension of the central axis of the mold, for example.

In the curing step, the formed cloth prepregs are cured by heat and pressure. A typical example of the method of curing the cloth prepregs is an autoclave molding method using a high-pressure furnace. This step can achieve uniform curing of the cloth prepregs.

In the demolding step, the cured cloth prepregs are allowed to cool to room temperature, and then extracted from the mold. This process can yield the tubular segment 122.

The bottom segment 123 is then fabricated by the same method as the method of fabricating the bottom segment 133. The fabricated bottom segment 123 is bonded to the tubular segment 122, thereby yielding the second tubular container 22. The bottom segment 123 can be bonded to the tubular segment 122 by the same method as the joining method between the bottom segment 133 and the tubular segment 132.

The description is then directed to a method of fabricating the tubular segment 122 containing woven fabrics and unidirectional fiber sheets as a base material.

The method of fabricating the tubular segment 122 containing woven fabrics and unidirectional fiber sheets as a base material involves a prepreg fabricating step of fabricating cloth prepregs containing woven fabrics as a base material and UD prepregs containing unidirectional fiber sheets as a base material, a first cloth prepreg forming step of attaching a cloth prepreg on the surface of a mold for defining the shape of the tubular segment 122 such that the direction of the warps or wefts of the woven fabric is orthogonal to the direction of extension of the central axis of the mold and thus forming the shape of the cloth prepreg, a UD prepreg forming step of attaching a UD prepreg on the formed cloth prepreg such that the direction of the fibers of the unidirectional fiber sheet is orthogonal to the direction of extension of the central axis of the mold and thus forming the shape of the UD prepreg, a second cloth prepreg forming step of attaching a cloth prepreg on the formed UD prepreg such that the direction of the warps or wefts of the woven fabric is orthogonal to the direction of extension of the central axis of the mold and thus forming the shape of the cloth prepreg, a curing step of curing the stacked prepregs, and a demolding step of extracting the cured prepregs from the mold.

In the prepreg fabricating step, woven fabrics are impregnated with a resin, and unidirectional fiber sheets are impregnated with a resin. The woven fabrics and the unidirectional fiber sheets are then heated. The heating period and the heating temperature can be appropriately determined depending on conditions, such as a type of the resin and an amount of the resin (resin amount) adhering to the woven fabrics or the unidirectional fiber sheets. In an exemplary case where the applied resin is an epoxy resin composition and the resin amount is 20 to 50 wt %, the heating period is determined to be 1 to 12 hours and the heating temperature is determined to be 80° C. to 150° C.

In the first cloth prepreg forming step, the cloth prepreg is cut in accordance with the size of the mold. The cut cloth prepreg is attached on the mold to form the shape. The cloth prepreg is attached to form the shape such that the direction of the warps or wefts of the woven fabric is orthogonal to the direction of extension of the central axis of the mold.

In the UD prepreg forming step, the UD prepreg is attached on the formed cloth prepreg to form the shape such that the direction of the fibers of the unidirectional fiber sheet is orthogonal to the direction of extension of the central axis of the mold. The area of the UD prepreg attached and formed on the cloth prepreg is preferably at least the area corresponding to the predetermined area 111 of the tubular segment 122. The UD prepreg is preferably attached on the whole area of the cloth prepreg to form the shape, in terms of enhancing the rigidity of the tubular segment 122 and in terms of avoiding deformation of the tubular segment 122.

In the second cloth prepreg forming step, the cloth prepreg is cut in accordance with the size of the mold. The cut cloth prepreg is attached on the formed UD prepreg to form the shape. The cloth prepreg is attached to form the shape such that the direction of the warps or wefts of the woven fabric is orthogonal to the direction of extension of the central axis of the mold.

In the curing step, the prepreg is cured by heat and pressure. A typical example of the method of curing the formed prepregs is an autoclave molding method using a high-pressure furnace. This step can achieve uniform curing of the prepregs.

In the demolding step, the prepregs are cooled to room temperature and then extracted from the mold. This process can yield the tubular segment 122.

The tubular segment 122 containing unidirectional fiber sheets as a base material can be fabricated by the above-described method of fabricating the tubular segment 122 containing woven fabrics and unidirectional fiber sheets as a base material except for the steps related to woven fabrics.

In the case where the predetermined area 111 and the other areas of the tubular segment 122 have different structures, a fabrication method that can provide a desired structure is preferably applied to the predetermined area 111, and a combination of fabrication methods that can provide desired structures is preferably applied to the other areas within the possible range.

Method of Fabricating the Outer Container 14

In the method of fabricating the outer container 14, a first portion surrounding the first tubular container 13, a second portion surrounding the second tubular container 22, and a third portion surrounding the bottom segment 123 are prepared separately.

The description is first directed to an example of the method of fabricating the first portion. In the case where the base material of the FRP contains woven fabrics, the method of fabricating the first portion involves a cloth prepreg fabricating step of fabricating cloth prepregs containing woven fabrics as a base material, a cloth prepreg forming step of attaching cloth prepregs on the surface of a mold for defining the shape of the outer container 14 surrounding the first tubular container 13 and thus forming the shape of the cloth prepregs, a curing step of curing the stacked cloth prepregs by heat and pressure, and a demolding step of extracting the cured cloth prepregs from the mold.

In the cloth prepreg fabricating step, woven fabrics serving as a base material are impregnated with a resin. The woven fabrics are then heated. The heating period and the heating temperature can be appropriately determined depending on conditions, such as a type of the resin and an amount of the resin (resin amount) adhering to the woven fabrics. In an exemplary case where the applied resin is an epoxy resin composition and the resin amount is 20 to 50 wt %, the heating period is determined to be 1 to 12 hours and the heating temperature is determined to be 80° C. to 150° C.

In the cloth prepreg forming step, the cloth prepregs are cut in accordance with the size of the mold. The cut cloth prepregs are attached on the mold to form the shape.

In the curing step, the formed cloth prepregs are cured by heat and pressure. A typical example of the method of curing the cloth prepregs is an autoclave molding method using a high-pressure furnace. This step can achieve uniform curing of the cloth prepregs.

In the demolding step, the cured cloth prepregs are allowed to cool to room temperature, and then extracted from the mold. This process can yield the first portion.

The description is then directed to an example of the method of fabricating the second portion of the outer container 14. In the case where the base material in the second portion contains woven fabrics, the fabrication method involves a cloth prepreg fabricating step of fabricating cloth prepregs containing woven fabrics as a base material, a first cloth prepreg forming step of attaching a cloth prepreg on the surface of a mold for defining the shape of the second portion of the outer container 14 surrounding the second tubular container 22 such that the direction of the warps or wefts of the woven fabric is parallel to the direction of extension of the central axis of the mold and thus forming the shape of the cloth prepreg, a honeycomb sheet stacking step of stacking the honeycomb sheet 70 on the predetermined area 112 of the attached and formed cloth prepreg, a second cloth prepreg forming step of attaching a cloth prepreg on the stacked honeycomb sheet 70 and on the cloth prepreg attached and formed in the first cloth prepreg forming step such that the direction of the warps or wefts of the woven fabric is parallel to the direction of extension of the central axis of the mold and thus forming the shape of the cloth prepreg, a curing step of curing the stacked cloth prepregs, and a demolding step of extracting the cured cloth prepregs from the mold.

In the cloth prepreg fabricating step, woven fabrics serving as a base material are impregnated with a resin. The woven fabrics are then heated. The heating period and the heating temperature can be appropriately determined depending on conditions, such as a type of the resin and an amount of the resin (resin amount) adhering to the woven fabrics. In an exemplary case where the applied resin is an epoxy resin composition and the resin amount is 20 to 50 wt %, the heating period is determined to be 1 to 12 hours and the heating temperature is determined to be 80° C. to 150° C.

In the first cloth prepreg forming step, the cloth prepreg is cut in accordance with the shape of the second portion of the outer container 14. The cut cloth prepreg is attached on the mold to form the shape. The cloth prepreg is attached to form the shape such that the direction of the warps or wefts of the woven fabric is parallel to the direction of extension of the central axis of the mold. Alternatively, the cloth prepreg may be attached to form the shape while being fed with hot air at a temperature of 50° C. to 100° C.

In the honeycomb sheet stacking step, the honeycomb sheet 70 is stacked on the area of the cloth prepreg planned to become the predetermined area 112.

In the second cloth prepreg forming step, the cloth prepreg is attached to form the shape on the attached honeycomb sheet 70 and the formed cloth prepreg, so as to follow the shape of the mold. The cloth prepreg is attached to form the shape such that the direction of the warps or wefts of the woven fabric is parallel to the direction of extension of the central axis of the mold. Alternatively, the cloth prepreg may be attached to form the shape while being fed with hot air at a temperature of 50° C. to 100° ° C.

In the curing step, the stacked cloth prepregs are cured by heat and pressure. A typical example of the method of curing the cloth prepregs is an autoclave molding method using a high-pressure furnace. This step can achieve uniform curing of the cloth prepregs.

In the demolding step, the cured cloth prepregs are allowed to cool to room temperature, and then extracted from the mold. This process can provide the outer container 14 surrounding the second tubular container 22.

The description is then directed to an example of the method of fabricating the second portion containing woven fabrics and unidirectional fiber sheets as a base material. This fabrication method involves a prepreg fabricating step of fabricating cloth prepregs containing woven fabrics as a base material and UD prepregs containing unidirectional fiber sheets as a base material, a first cloth prepreg forming step of attaching a cloth prepreg on the surface of a mold for defining the shape of the second portion of the outer container 14 surrounding the predetermined area 111 of the second tubular container 22 such that the direction of the warps or wefts of the woven fabric is parallel to the direction of extension of the central axis of the mold and thus forming the shape of the cloth prepreg, a honeycomb sheet stacking step of stacking a honeycomb sheet on the predetermined area 112 of the formed cloth prepreg, a second cloth prepreg forming step of attaching a cloth prepreg on the stacked honeycomb sheet and the cloth prepreg attached and formed in the first cloth prepreg forming step such that the direction of the warps or wefts of the woven fabric is parallel to the direction of extension of the central axis of the mold and thus forming the shape of the cloth prepreg, a UD prepreg forming step of attaching a UD prepreg on the formed cloth prepreg such that the direction of the fibers of the unidirectional fiber sheet is parallel to the direction of extension of the central axis of the mold and thus forming the shape of the UD prepreg, a curing step of curing the stacked prepregs, and a demolding step of extracting the cured prepregs from the mold.

In the prepreg fabricating step, woven fabrics and unidirectional fiber sheets are each impregnated with a resin and then heated, thereby producing cloth prepregs and UD prepregs cured in the B-stage. The heating period and the heating temperature can be appropriately determined depending on conditions, such as a type of the resin and an amount of the resin (resin amount) adhering to the woven fabrics or the unidirectional fiber sheets. In an exemplary case where the applied resin is an epoxy resin composition and the resin amount is 20 to 50 wt %, the heating period is determined to be 1 to 12 hours and the heating temperature is determined to be 80° C. to 150° C.

In the first cloth prepreg forming step, the cloth prepreg is cut in accordance with the size of the mold. The cut cloth prepreg is attached on the mold to form the shape. The cloth prepreg is attached to form the shape such that the direction of the warps or wefts of the woven fabric is parallel to the direction of extension of the central axis of the mold, for example. Alternatively, the cloth prepreg may be attached to form the shape while being fed with hot air at a temperature of 50° C. to 100° C.

In the honeycomb sheet stacking step, the honeycomb sheet 70 is stacked on the area of the cloth prepreg planned to become the predetermined area 112.

In the second cloth prepreg forming step, the cloth prepreg is cut in accordance with the size of the mold. The cut cloth prepreg is attached on the honeycomb sheet 70 and the formed cloth prepreg to form the shape. The cloth prepreg is attached to form the shape such that the direction of the warps or wefts of the woven fabric is parallel to the direction of extension of the central axis of the mold, for example. Alternatively, the cloth prepreg may be attached to form the shape while being fed with hot air at a temperature of 50° ° C. to 100° ° C.

In the UD prepreg forming step, the UD prepreg is attached on the formed cloth prepreg to form the shape such that the direction of the fibers of the unidirectional fiber sheet is parallel to the direction of extension of the central axis of the mold, for example. The area of the UD prepreg attached and formed on the cloth prepreg is preferably at least the area corresponding to the predetermined area 112 of the outer container 14. The UD prepreg is preferably attached and formed on the whole area of the outer container 14, in terms of enhancing the rigidity of the outer container 14 and in terms of avoiding deformation of the outer container 14.

In the curing step, the stacked prepregs are cured by heat and pressure. A typical example of the method of curing the prepregs is an autoclave molding method using a high-pressure furnace. This step can achieve uniform curing of the prepregs.

In the demolding step, the prepregs are cooled to room temperature and then extracted from the mold. This process can yield the second portion of the outer container 14.

The third portion of the outer container 14 can be fabricated by the same method as the method of fabricating the bottom segment 123. Then, the first portion and the third portion of the outer container 14 are air-tightly bonded to each other. The joining method is the same as the joining method between the bottom segment 123 and the tubular segment 122.

The components fabricated as described above are joined to each other, thereby completing the thermally insulated container 10. Specifically, the second tubular container 22 is air-tightly bonded to the tubular segment 132 of the first tubular container 13. The refrigerant inlet tube 12 is then air-tightly bonded to the first tubular container 13. The first portion, the second portion, and the third portion of the outer container 14 are then disposed so as to surround the inner container 11 and air-tightly bonded to each other.

Then, the air inside the void 15 is discharged with a vacuum pump, for example, via an air vent preliminarily or recently provided. When the pressure inside the vacuumed void 15 reaches the reference value or lower, the air vent is air-tightly closed with a resin, for example. The above-described process completes the thermally insulated container 10. The individual components can be joined by the same method as the joining method between the bottom segment 123 and the tubular segment 122.

The above-described thermally insulated container 10 according to Embodiment 1 can be applied as a thermally insulated container for use in the medial field, for example. The following description is directed to an exemplary application of the thermally insulated container 10.

Exemplary Application 1

The thermally insulated container 10 is typically applied to a magnetospinograph 60, for example.

Figure 9:
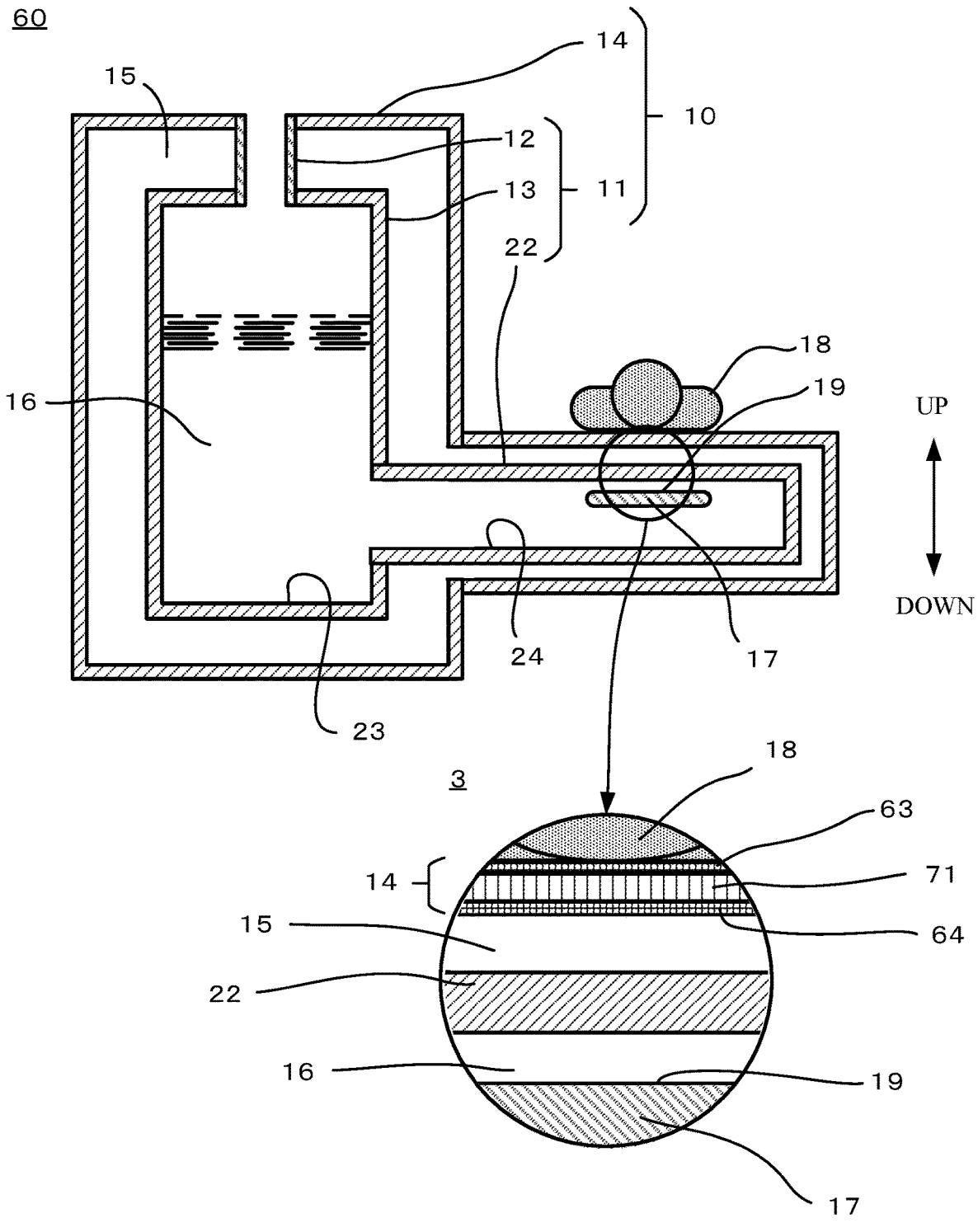
FIG. 9 is a schematic sectional view of a magnetospinograph including the thermally insulated container according to the embodiment of the present disclosure.

As illustrated in FIG. 9, the magnetospinograph 60 includes a superconducting quantum interference device 17 to detect magnetic fields generated from a living body 18, and the thermally insulated container 10. The thermally insulated container 10 includes the inner container 11, and the outer container 14 surrounding the inner container 11 via the void 15. The inner container 11 includes the first tubular container 13 having the internal holder 23 for reserving the refrigerant 16, the refrigerant inlet tube 12 fixed to the first tubular container 13, and the second tubular container 22 having the internal holder 24 for reserving the refrigerant 16. The superconducting quantum interference device 17 is accommodated in the second tubular container 22 while being immersed in the refrigerant 16 reserved in the second tubular container 22. As illustrated in FIG. 9, the living body 18 lies such that the spinal cord of the living body 18 is located above a measurement surface 19 of the superconducting quantum interference device 17.

As illustrated in the enlarged view in the circle 3 of FIG. 9, the predetermined area of the outer container 14 has a structure in which a woven fabric 63 is stacked on one surface of a honeycomb sheet 71 and a woven fabric 64 is stacked on the other surface. The superconducting quantum interference device 17 is accommodated in the second tubular container 22 while being immersed in the refrigerant 16. The measurement surface 19 is opposed to the honeycomb sheet 71.

The base material in the predetermined area 112 of the outer container 14 may contain the woven fabric 63 and a unidirectional fiber sheet. In this structure, the unidirectional fiber sheet is disposed between the honeycomb sheet 71 and the woven fabric 63. Alternatively, the unidirectional fiber sheet may be stacked on the woven fabric 63. Alternatively, the unidirectional fiber sheet may be disposed between the honeycomb sheet 71 and the woven fabric 64. Alternatively, the unidirectional fiber sheet may be disposed under the woven fabric 64. The unidirectional fiber sheet is preferably stacked such that the direction of the fibers is parallel to the direction of extension of the central axis of the second tubular container 22, in terms of ensuring the rigidity of the outer container 14, and in terms of avoiding deformation of the outer container 14 caused by external pressures and external stresses.

The base material in the predetermined area 111 of the second tubular container 22 may contain a woven fabric and a unidirectional fiber sheet. The unidirectional fiber sheet is preferably stacked such that the direction of the fibers is orthogonal to the direction of extension of the central axis of the second tubular container 22, in terms of ensuring the rigidity of the predetermined area 111 of the second tubular container 22, and in terms of avoiding deformation of the second tubular container 22 caused by internal pressures.

In the case where the base material in the predetermined area 112 of the outer container 14 contains a unidirectional fiber sheet, the measurement surface 19 of the superconducting quantum interference device 17 is opposed to a surface of the unidirectional fiber sheet in the predetermined area 112 of the outer container 14. In the case where the base material in the predetermined area 111 of the second tubular container 22 contains a unidirectional fiber sheet, the measurement surface 19 of the superconducting quantum interference device 17 is opposed to a surface of the unidirectional fiber sheet in the predetermined area 111 of the second tubular container 22.

Effects

The thermally insulated container 10 and the magnetospinograph 60 including the thermally insulated container 10 can bring about the following effects.

In the thermally insulated container 10, the base material in the predetermined area 112 of the outer container 14 contains the woven fabric 63 and the woven fabric 64, and contains the honeycomb sheet 71 in the predetermined area 112 of the outer container 14. The woven fabric 63 is stacked on one surface of the honeycomb sheet 71, and the woven fabric 64 is stacked on the other surface. This structure can improve the thermal insulation properties of the thermally insulated container 10.

The base material in the predetermined area 112 of the outer container 14 further containing a unidirectional fiber sheet can ensure the rigidity of the outer container 14. The outer container 14 surrounds the second tubular container 22 such that the unidirectional fiber sheet in the predetermined area 112 of the outer container 14 is opposed to the unidirectional fiber sheet in the predetermined area 111 of the second tubular container 22. This structure can allow the thermally insulated container 10 to have sufficient rigidity to resist external stresses and internal and external pressures, despite of the vacuum state of the void 15.

Since the base material in the predetermined area 111 of the second tubular container 22 and the base material in the predetermined area 112 of the outer container 14 contain unidirectional fiber sheets that can provide high rigidity against stresses, the predetermined area 111 of the second tubular container 22 and the predetermined area 112 of the outer container 14 can achieve rigidity. That is, a structure containing both of woven fabrics and unidirectional fiber sheets can achieve the same rigidity as the rigidity achievable by a structure containing woven fabrics alone, despite of thinner walls than the structure containing woven fabrics alone. The magnetospinograph 60 including the thermally insulated container 10 can thus achieve a reduced distance (lift-off) from the measurement surface 19 of the superconducting quantum interference device 17 to the spinal cord (measurement target site) of the living body 18.

Furthermore, the magnetospinograph 60 including the thermally insulated container 10 provided with the refrigerant inlet tube 12 can reduce heat conduction from the outside via the refrigerant inlet tube 12 to the first tubular container 13 and the second tubular container 22. The thermally insulated container 10 is thus able to reserve the refrigerant 16 for a long period, thereby extending the operating period of the magnetospinograph 60.

Examples

In order to evaluate the thermal insulation properties of the outer container 14 included in the thermally insulated container 10, samples were fabricated in accordance with the structures of the examples and the comparative examples illustrated in Table 1, followed by measurement of the thermal conductivities of the samples. In addition, in order to evaluate differences in rigidity caused by different stacking structures of the walls of the outer container 14 and evaluate differences in rigidity caused by different stacking structures of the walls of the second tubular container 22, samples were fabricated in accordance with the structures of the examples and the comparative examples illustrated in Tables 1 and 2, followed by measurement of bending strengths and bending elastic moduli of the samples. These examples are not intended to limit the scope of the present disclosure.

The resins, the base materials, and the honeycomb sheets used in the examples and the comparative examples are as follows.

Resins (1) Matrix resin A (1-1) Base resin: bisphenol A epoxy resin (DER383LCL, manufactured by The Dow Chemical Company)

(1-2) Curing agent: acid anhydride curing agent (HN-2000, manufactured by Hitachi Chemical Co., Ltd.)

(1-3) Curing accelerator: N, N-dimethylbenzylamine (Kaolizer No. 20, manufactured by Kao Corporation)

(2) Matrix resin B (2-1) Base resin: bisphenol A epoxy resin (EPICLON850, manufactured by DIC Corporation)

(2-2) Curing agent: amine curing agent (DICY, manufactured by Nippon Carbide Industries Co., Inc.)

(2-3) Curing accelerator: dimethylbenzylamine (Kaolizer No. 20, manufactured by Kao Corporation)

Base Materials and Honeycomb Sheets (1) Woven fabric (glass): glass cloth (ECC75 181, manufactured by Arisawa Fiber Glass Co., Ltd.)

(2) Woven fabric (alumina): alumina cloth (ALPT5107, manufactured by Arisawa Mfg. Co., Ltd.)

(3) Woven fabric (carbon): carbon cloth (CFPH3113, manufactured by Arisawa Mfg. Co., Ltd.)

(4) UD sheet (alumina): unidirectional fiber sheet containing alumina fibers (UDP-AL/CR8, manufactured by Arisawa Mfg. Co., Ltd.)

(5) UD sheet (glass): unidirectional fiber sheet containing glass fibers (UDP-GF/CR8, manufactured by Arisawa Mfg. Co., Ltd.)

(6) UD sheet (carbon): unidirectional fiber sheet containing carbon fibers (UDP-CF/CR8, manufactured by Arisawa Mfg. Co., Ltd.)

(7) Honeycomb sheet A (Honeycomb core, manufactured by Tasuns Composite Technology Co., Ltd.) having a thickness of 1.2 mm (8) Honeycomb sheet B (Honeycomb core, manufactured by Tasuns Composite Technology Co., Ltd.) having a thickness of 7.0 mm Resins to be impregnated in the base materials were prepared.

(1) Preparation of Resins (1-1) Preparation of a Resin to be Applied to Prepregs Containing Woven Fabrics as a Base Material The base resin, the curing agent, and the curing accelerator of the matrix resin A were used. First, 100 parts by weight of the base resin, 88 parts by weight of the curing agent, and 0.8 parts by weight of the curing accelerator were added to a vessel. The mixture was then stirred with a high-speed mixer at room temperature at a rate of 700 rpm for 60 minutes, thereby yielding the matrix resin A. The resulting viscosity was 500 mPa s.

(1-2) Preparation of a Resin to be Applied to Prepregs Containing UD Sheets as a Base Material The base resin, the curing agent, and the curing accelerator of the matrix resin B were used. First, 100 parts by weight of the base resin, 88 parts by weight of the curing agent, and 0.8 parts by weight of the curing accelerator were added to a vessel. The mixture was then stirred with a high-speed mixer at room temperature at a rate of 700 rpm for 60 minutes, thereby yielding the matrix resin B. The resulting viscosity was 500 mPa s.

Prepregs were fabricated using the prepared resins.

(2) Fabrication of Prepregs (2-1) Fabrication of Cloth Prepregs Containing Woven Fabrics as a Base Material The woven fabrics were impregnated with the matrix resin A so as to achieve a resin amount of 35 wt % after curing. The woven fabrics were then dried at a temperature of 130° ° C. for ten minutes, thereby yielding prepregs cured in the B-stage having a resin amount of 35 wt %.

(2-2) Fabrication of UD Prepregs Containing UD Sheets as a Base Material

The UD sheets were impregnated with the matrix resin B so as to achieve a resin amount of 35 wt % after curing. The UD sheets were then dried at a temperature of 130° C. for ten minutes, thereby yielding UD prepregs cured in the B-stage having a resin amount of 35 wt %.

The following description is directed to a method of fabricating measurement samples and methods of measurement and evaluation.

(3) Fabrication of Measurement Samples for Evaluation of the Walls of the Outer Container 14

The measurement samples for measurement of thermal conductivities, bending strengths, and bending elastic moduli of the walls of the outer container 14 were fabricated as follows. First, the prepregs fabricated as described in (2-1) and (2-2) and the honeycomb sheets were stacked on each other so as to have the same stacking structures as the stacking structures of Examples 1 to 10 and Comparative Example 1 illustrated in Table 1. Each of the cloth prepregs was stacked such that the warps formed a predetermined angle from any one reference side of the undermost prepreg. Each of the UD prepregs was stacked such that the fibers of the UD prepreg formed a predetermined angle from the reference side of the undermost prepreg used as a reference in stacking of the cloth prepreg. The predetermined angle corresponds to the angles listed in the examples and the comparative examples illustrated in Table 1. The stacked prepregs were then pressed at a temperature of 130° ° C. at a pressure of 0.29 MPa for 90 minutes, so as to achieve a resin amount of 35 wt % after curing and a thickness of 2.5 mm after curing. This pressing step produced measurement samples cured in the C-stage.

The measurement samples for measurement of bending strengths and bending elastic moduli were cut and adjusted so as to have a rectangular shape having a width of 10 mm and a length of 20 mm. The measurement samples in Examples 1 to 4 and Comparative Example 1 were each cut such that the longitudinal direction of the measurement sample was parallel to the warps of the cloth prepregs in the measurement sample. The measurement samples in Examples 5 to 10 were each cut such that the longitudinal direction of the measurement sample was parallel to the fibers of the UD prepregs in the measurement sample. The cutting of the measurement samples in Examples 5 to 10 such that the longitudinal direction of the measurement sample was parallel to the fibers of the UD prepregs was aimed at appropriate evaluation of differences in effects (rigidity) caused by different directions of extension of fibers when the walls of the thermally insulated container 10 contain a unidirectional fiber sheet as a base material.

The measurement samples for measurement of thermal conductivities were provided by cutting the measurement samples having a flat plate shape and a thickness of 2.5 mm, which were fabricated for measurement of thermal conductivities, bending strengths, and bending elastic moduli, into a circular shape having a diameter of 50 mm.

(4) Fabrication of Measurement Samples for Evaluation of the Walls of the Second Tubular Container 22

The measurement samples for measurement of bending strengths and bending elastic moduli of the walls of the second tubular container 22 were fabricated as follows. The prepregs fabricated as described in (2-1) and (2-2) were stacked on each other so as to have the same stacking structures as the stacking structures of Examples 11 to 18 illustrated in Table 2. Each of the cloth prepregs was stacked such that the warps formed a predetermined angle from any one reference side of the undermost prepreg. Each of the UD prepregs was stacked such that the fibers of the UD prepreg formed a predetermined angle from the reference side of the undermost prepreg used as a reference in stacking of the cloth prepreg. The predetermined angle corresponds to the angles listed in the examples illustrated in Table 2. The stacked prepregs were pressed at a temperature of 130° ° C. at a pressure of 0.29 MPa for 90 minutes, so as to achieve a resin amount of 35 wt % after curing and a thickness of 2.5 mm after curing. This pressing step produced measurement samples cured in the C-stage. The resulting measurement samples were then cut so as to have a rectangular shape having a width of 10 mm and a length of 20 mm. The measurement samples in Examples 11 to 13 were each cut such that the longitudinal direction of the measurement sample was parallel to the warps of the cloth prepregs in the measurement samples. The measurement samples in Examples 14 to 18 were each cut such that the longitudinal direction of the measurement sample was parallel to the fibers of the UD prepregs in the measurement samples.

(5) Measurement of Thermal Conductivities

The thermal conductivities (W/m K) were measured with a measurement device (ARC-TC-1000, manufactured by AGNE Gijutsu Center Inc.). The measurement uses a temperature-gradient method. The measurement conditions are pursuant to ASTME1225.

(6) Measurement of Bending Strengths and Bending Elastic Moduli

The bending strengths and the bending elastic moduli of the measurement samples were measured with an autograph tester (AG-10, manufactured by Shimadzu Corporation). The measurement is based on a three-point bending test (distance between supports of 10 mm, testing rate of 2 mm/min). Before measurement, a measurement sample was installed in the tester such that both supports of the three-point bending test were located at both ends of the measurement sample in its longitudinal direction. The bending strengths and the bending elastic moduli were calculated from the resulting maximum bending stresses (breaking load) in accordance with JIS K7017.

Table 1 illustrates results of measurement of the thermal conductivities, the bending strengths, and the bending elastic moduli in Examples 1 to 10 and Comparative Example 1. Table 2 illustrates results of measurement of the bending strengths and the bending elastic moduli in Examples 11 to 18.

TABLE 1

| ITEM | EXAMPLE 1 | EXAMPLE 2 | EXAMPLE 3 | EXAMPLE 4 | EXAMPLE 5 | EXAMPLE 6 |
|---|---|---|---|---|---|---|
| STACKING STRUCTURE OF OUTER CONTAINER(1): TYPE OF BASE MATERIAL (TYPE OF FIBERS) ANGLE(2)(3) | WOVEN FABRIC (GLASS) 0° | WOVEN FABRIC (ALUMINA) 0° | WOVEN FABRIC (CARBON) 0° | WOVEN FABRIC (GLASS) 0° | UD (ALUMINA) 0° | UD (ALUMINA) 0° |
| | WOVEN FABRIC (GLASS) 0° | WOVEN FABRIC (ALUMINA) 0° | WOVEN FABRIC (CARBON) 0° | WOVEN FABRIC (GLASS) 0° | UD (ALUMINA) 0° | UD (ALUMINA) 0° |
| | WOVEN FABRIC (GLASS) 0° | WOVEN FABRIC (ALUMINA) 0° | WOVEN FABRIC (CARBON) 0° | WOVEN FABRIC (GLASS) 0° | WOVEN FABRIC (GLASS) 0° | WOVEN FABRIC (GLASS) 0° |
| | WOVEN FABRIC (GLASS) 0° | WOVEN FABRIC (ALUMINA) 0° | WOVEN FABRIC (CARBON) 0° | WOVEN FABRIC (GLASS) 0° | WOVEN FABRIC (GLASS) 0° | WOVEN FABRIC (GLASS) 0° |
| | HONEYCOMB SHEET A | HONEYCOMB SHEET A | HONEYCOMB SHEET A | HONEYCOMB SHEET B | HONEYCOMB SHEET A | HONEYCOMB SHEET A |
| | WOVEN FABRIC (GLASS) 0° | WOVEN FABRIC (ALUMINA) 0° | WOVEN FABRIC (CARBON) 0° | WOVEN FABRIC (GLASS) 0° | WOVEN FABRIC (GLASS) 0° | WOVEN FABRIC (GLASS) 0° |
| | WOVEN FABRIC (GLASS) 0° | WOVEN FABRIC (ALUMINA) 0° | WOVEN FABRIC (CARBON) 0° | WOVEN FABRIC (GLASS) 0° | WOVEN FABRIC (GLASS) 0° | WOVEN FABRIC (GLASS) 0° |
| | WOVEN FABRIC (GLASS) 0° | WOVEN FABRIC (ALUMINA) 0° | WOVEN FABRIC (CARBON) 0° | WOVEN FABRIC (GLASS) 0° | UD (ALUMINA) 0° | WOVEN FABRIC (GLASS) 0° |
| | WOVEN FABRIC (GLASS) 0° | WOVEN FABRIC (ALUMINA) 0° | WOVEN FABRIC (CARBON) 0° | WOVEN FABRIC (GLASS) 0° | UD (ALUMINA) 0° | WOVEN FABRIC (GLASS) 0° |
| THERMAL CONDUCTIVITY (W/mK) | 0.10 | 0.14 | 0.31 | 0.08 | 0.14 | 0.15 |
| BENDING STRENGTH (MPa) | 36 | 48 | 62 | 40 | 125 | 120 |
| BENDING ELASTIC MODULUS (GPa) | 4 | 6 | 8 | 12 | 16 | 14 |

| ITEM | EXAMPLE 7 | EXAMPLE 8 | EXAMPLE 9 | EXAMPLE 10 | COMPARATIVE EXAMPLE 1 |
|---|---|---|---|---|---|
| STACKING STRUCTURE OF OUTER CONTAINER(1): TYPE OF BASE MATERIAL (TYPE OF FIBERS) ANGLE(2)(3) | UD (GLASS) 0° | UD (CARBON) 0° | WOVEN FABRIC (GLASS) 0° | UD (ALUMINA) 0° | WOVEN FABRIC (GLASS) 0° |
| | UD (GLASS) 0° | UD (CARBON) 0° | UD (ALUMINA) 0° | WOVEN FABRIC (GLASS) 0° | WOVEN FABRIC (GLASS) 0° |
| | WOVEN FABRIC (GLASS) 0° | WOVEN FABRIC (GLASS) 0° | WOVEN FABRIC (GLASS) 0° | UD (ALUMINA) 0° | WOVEN FABRIC (GLASS) 0° |
| | WOVEN FABRIC (GLASS) 0° | WOVEN FABRIC (GLASS) 0° | WOVEN FABRIC (GLASS) 0° | WOVEN FABRIC (GLASS) 0° | WOVEN FABRIC (GLASS) 0° |
| | HONEYCOMB SHEET A | HONEYCOMB SHEET A | HONEYCOMB SHEET A | HONEYCOMB SHEET A | WOVEN FABRIC (GLASS) 0° |
| | WOVEN FABRIC (GLASS) 0° | WOVEN FABRIC (GLASS) 0° | WOVEN FABRIC (GLASS) 0° | WOVEN FABRIC (GLASS) 0° | WOVEN FABRIC (GLASS) 0° |

TABLE 1-continued

| | | WOVEN FABRIC (GLASS) 0° / UD (GLASS) 0° / UD (GLASS) 0° | WOVEN FABRIC (GLASS) 0° / UD (CARBON) 0° / UD (CARBON) 0° | WOVEN FABRIC (GLASS) 0° / UD (ALUMINA) 0° / WOVEN FABRIC (GLASS) 0° | UD (ALUMINA) 0° / WOVEN FABRIC (GLASS) 0° / UD (ALUMINA) 0° | WOVEN FABRIC (GLASS) 0° / WOVEN FABRIC (GLASS) 0° / WOVEN FABRIC (GLASS) 0° |
|---|---|---|---|---|---|---|
| | THERMAL CONDUCTIVITY (W/mK) | 0.16 | 0.28 | 0.14 | 0.14 | 0.53 |
| | BENDING STRENGTH (MPa) | 70 | 405 | 178 | 314 | 585 |
| | BENDING ELASTIC MODULUS (GPa) | 10 | 30 | 22 | 15 | 22 |

[1] The stacking structure indicates a structure of the layers of the base material, and UD indicates a unidirectional fiber sheet.
[2] The angle of a woven fabric indicates an angle formed between the warps and one side of the undermost prepreg.
[3] The angle of a UD sheet indicates an angle formed between the fibers of the UD and one side of the undermost prepreg.

TABLE 2

| ITEM | EXAMPLE 11 | EXAMPLE 12 | EXAMPLE 13 | EXAMPLE 14 | EXAMPLE 15 | EXAMPLE 16 | EXAMPLE 17 | EXAMPLE 18 |
|---|---|---|---|---|---|---|---|---|
| STACKING STRUCTURE OF SECOND TUBULAR CONTAINER[1]: TYPE OF BASE MATERIAL (TYPE OF FIBERS) ANGLE[2][3] | WOVEN FABRIC (GLASS) 0° | WOVEN FABRIC (ALUMINA) 0° | WOVEN FABRIC (CARBON) 0° | WOVEN FABRIC (GLASS) 0° | WOVEN FABRIC (GLASS) 0° | WOVEN FABRIC (GLASS) 0° | UD (ALUMINA) 90° | UD (ALUMINA) 90° |
| | WOVEN FABRIC (GLASS) 0° | WOVEN FABRIC (ALUMINA) 0° | WOVEN FABRIC (CARBON) 0° | WOVEN FABRIC (GLASS) 0° | WOVEN FABRIC (GLASS) 0° | WOVEN FABRIC (GLASS) 0° | UD (ALUMINA) 90° | WOVEN FABRIC (GLASS) 0° |
| | WOVEN FABRIC (GLASS) 0° | WOVEN FABRIC (ALUMINA) 0° | WOVEN FABRIC (CARBON) 0° | WOVEN FABRIC (GLASS) 0° | WOVEN FABRIC (GLASS) 0° | WOVEN FABRIC (GLASS) 0° | WOVEN FABRIC (GLASS) 0° | UD (ALUMINA) 90° |
| | WOVEN FABRIC (GLASS) 0° | WOVEN FABRIC (ALUMINA) 0° | WOVEN FABRIC (CARBON) 0° | WOVEN FABRIC (GLASS) 0° | WOVEN FABRIC (GLASS) 0° | WOVEN FABRIC (GLASS) 0° | WOVEN FABRIC (GLASS) 0° | WOVEN FABRIC (GLASS) 0° |
| | WOVEN FABRIC (GLASS) 0° | WOVEN FABRIC (ALUMINA) 0° | WOVEN FABRIC (CARBON) 0° | UD (ALUMINA) 90° | UD (GLASS) 90° | UD (CARBON) 90° | WOVEN FABRIC (GLASS) 0° | UD (ALUMINA) 90° |
| | WOVEN FABRIC (GLASS) 0° | WOVEN FABRIC (ALUMINA) 0° | WOVEN FABRIC (CARBON) 0° | WOVEN FABRIC (GLASS) 0° | WOVEN FABRIC (GLASS) 0° | WOVEN FABRIC (GLASS) 0° | WOVEN FABRIC (GLASS) 0° | WOVEN FABRIC (GLASS) 0° |
| | WOVEN FABRIC (GLASS) 0° | WOVEN FABRIC (ALUMINA) 0° | WOVEN FABRIC (CARBON) 0° | WOVEN FABRIC (GLASS) 0° | WOVEN FABRIC (GLASS) 0° | WOVEN FABRIC (GLASS) 0° | WOVEN FABRIC (GLASS) 0° | UD (ALUMINA) 90° |
| | WOVEN FABRIC (GLASS) 0° | WOVEN FABRIC (ALUMINA) 0° | WOVEN FABRIC (CARBON) 0° | WOVEN FABRIC (GLASS) 0° | WOVEN FABRIC (GLASS) 0° | WOVEN FABRIC (GLASS) 0° | UD (ALUMINA) 90° | WOVEN FABRIC (GLASS) 0° |
| | WOVEN FABRIC (GLASS) 0° | WOVEN FABRIC (ALUMINA) 0 | WOVEN FABRIC (CARBON) 0° | WOVEN FABRIC (GLASS) 0° | WOVEN FABRIC (GLASS) 0° | WOVEN FABRIC (GLASS) 0° | UD (ALUMINA) 90° | UD (ALUMINA) 90° |
| BENDING STRENGTH (MPa) | 585 | 780 | 1010 | 710 | 690 | 730 | 750 | 814 |
| BENDING ELASTIC MODULUS (GPa) | 22 | 30 | 38 | 30 | 28 | 33 | 49 | 43 |

[1] The stacking structure indicates a structure of the layers of the base material, and UD indicates a unidirectional fiber sheet.
[2] The angle of a woven fabric indicates an angle formed between the warps and one side of the undermost prepreg.
[3] The angle of a UD sheet indicates an angle formed between the fibers of the UD and one side of the undermost prepreg.

Comparison between the examples illustrated in Table 1 revealed that, for example, Example 1 was able to reduce the thermal conductivity by approximately 80% in comparison to Comparative Example 1. Example 8 was found to be able to reduce the thermal conductivity by approximately 50% while maintaining approximately 70% of the bending strength, in comparison to Comparative Example 1.

Comparison between the examples and the comparative example illustrated in Table 2 revealed that, for example, the bending strength in Example 13 was approximately 1.7 times as high as that in Example 11 on the assumption that the samples had the same thickness. The bending elastic modulus in Example 17 was found to be approximately 2.2 times as high as that in Example 11.

These measurement results imply that if the wall of the predetermined area 112 of the outer container 14 surrounding the second tubular container 22 has any of the stacking structures in Examples 1 to 10, the thermally insulated container 10 can achieve improved thermal insulation properties. If the wall of the predetermined area 111 of the second tubular container 22 has any of the stacking structures in Examples 11 to 18, the walls of the second tubular container 22 can achieve a reduced thickness while maintaining the rigidity equivalent to that of the walls of an existing thermally insulated container. The magnetospinograph 60 including this thermally insulated container 10 can therefore achieve a reduced distance (lift-off) from the measurement surface 19 of the superconducting quantum interference device 17 to the measurement target site of a spinal cord, and thus is able to measure ultraweak magnetic fields.

Accordingly, the above-described embodiment can provide a thermally insulated container characterized by excellent thermal insulation properties and thin walls, and a magnetospinograph including the thermally insulated container.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2021-090086, filed on May 28, 2021, the entire disclosure of which is incorporated by reference herein.

REFERENCE SIGNS LIST

10 Thermally insulated container
11 Inner container
12 Refrigerant inlet tube
13 First tubular container
131 Ceiling segment
122, 132 Tubular segment
123, 133 Bottom segment
132O Outer layer
132I Inner layer
111, 112 Predetermined area
101 Measurement target
102 Measurement device
14 Outer container
15 Void 16 Refrigerant
17 Superconducting quantum interference device
18 Living body
19 Measurement surface
21 Base material
22 Second tubular container
23, 24 Holder
60 Magnetospinograph
63, 64 Woven fabric
65 Holding yarn
66 Flat yarn
70, 71 Honeycomb sheet

The invention claimed is:
1. A magnetospinograph, comprising:
a superconducting quantum interference device to detect magnetic fields generated from a living body; and
a thermally insulated container, comprising:
an inner container; and
an outer container surrounding the inner container via a void, wherein
each of the inner container and the outer container is made of a fiber reinforced plastic prepared by impregnating a base material containing fibers with a resin,
the inner container includes:
a first tubular container and a second tubular container each including an internal holder to reserve a refrigerant, and
a refrigerant inlet tube through which the refrigerant is introduced into the first tubular container,
the outer container includes a first portion surrounding the first tubular container of the inner container and a second portion surrounding the second tubular container of the inner container, wherein the second portion of the outer container includes a predetermined area configured to receive a load of a measurement target,
the holder of the second tubular container is in communication with the holder of the first tubular container,
the base material in each of a predetermined area of the second tubular container and predetermined area of the second portion of the outer container contains woven fabrics,
the base material in the predetermined area of the second portion of the outer container further contains a honeycomb sheet, the predetermined area of the second portion of the outer container having a higher rigidity from the honeycomb sheet than the areas of the outer container other than the predetermined area of the second portion of the outer container and the first portion of the outer container such that the predetermined area is configured to receive the load of the measurement target, and
the woven fabrics are stacked on one and another surfaces of the honeycomb sheet,
wherein,
the superconducting quantum interference device is immersed in the refrigerant reserved in the holder of the second tubular container.
2. The magnetospinograph according to claim 1, wherein the woven fabrics contains at least one selected from the group consisting of glass fibers, alumina fibers, and carbon fibers.

3. The magnetospinograph according to claim 1, wherein the base material in the predetermined area of the outer container further contains a unidirectional fiber sheet fabricated by aligning multiple fibers to one direction, and the unidirectional fiber sheet is stacked on at least one of the one and the other surfaces of the honeycomb sheet.

4. The magnetospinograph according to claim 3, wherein a direction of the fibers of the unidirectional fiber sheet in the predetermined area of the outer container is parallel to a direction of extension of a central axis of the second tubular container.

5. The magnetospinograph according to claim 3, wherein the base material in the predetermined area of the second tubular container further contains a unidirectional fiber sheet fabricated by aligning multiple fibers to one direction.

6. The magnetospinograph according to claim 5, wherein a direction of the fibers of the unidirectional fiber sheet in the predetermined area of the second tubular container is orthogonal to a direction of extension of a central axis of the second tubular container.

7. The magnetospinograph according to claim 5, wherein the outer container surrounds the second tubular container such that the unidirectional fiber sheet in the predetermined area of the outer container is opposed to the unidirectional fiber sheet in the predetermined area of the second tubular container.

8. The magnetospinograph according to claim 3, wherein the unidirectional fiber sheet in the predetermined area of the outer container contains at least one selected from the group consisting of glass fibers, alumina fibers, and carbon fibers.

9. The magnetospinograph according to claim 5, wherein the unidirectional fiber sheet in the predetermined area of the second tubular container contains at least one selected from the group consisting of glass fibers, alumina fibers, and carbon fibers.

10. The magnetospinograph according to claim 1, wherein the honeycomb sheet has a thickness of 1 to 7 mm.

11. The magnetospinograph according to claim 1, wherein the resin contains an epoxy resin.

12. The magnetospinograph according to claim 1, wherein the honeycomb sheet includes hexagonal cells, wherein each side of the hexagonal cells has a length of 3 to 10 mm.

13. The magnetospinograph according to claim 12, wherein the length is 3 to 5 mm.

14. The magnetospinograph according to claim 1, wherein the fabric is stacked and attached on one surface and the other surface of the honeycomb sheet.

15. The magnetospinograph according to claim 1, and a measurement surface of the superconducting quantum interference device faces the predetermined area of the second tubular container and the predetermined area of the second portion of the outer container.

16. The magnetospinograph according to claim 1, wherein the second tubular container includes a portion having an axis disposed horizontally and a bottom surface portion closing one end portion of the cylindrical portion, and the second portion of the outer container extends laterally from the first portion of the outer container.

17. The magnetospinograph according to claim 1, wherein the first portion of the outer container has a longitudinal axis and the second portion of the outer container extends laterally from the first potion of the outer container.

18. A thermally insulated container, comprising:

an inner container; and an outer container surrounding the inner container via a void, wherein each of the inner container and the outer container is made of a fiber reinforced plastic prepared by impregnating a base material containing fibers with a resin, the inner container includes:

a first tubular container and a second tubular container each including an internal holder to reserve a refrigerant, and a refrigerant inlet tube through which the refrigerant is introduced into the first tubular container, the outer container includes a first portion surrounding the first tubular container of the inner container and a second portion surrounding the second tubular container of the inner container, wherein the second portion of the outer container includes a predetermined area configured to receive a load of a measurement target, the holder of the second tubular container is in communication with the holder of the first tubular container, the base material in each of a predetermined area of the second tubular container and predetermined area of the second portion of the outer container contains woven fabrics, the base material in the predetermined area of the second portion of the outer container further contains a honeycomb sheet, the predetermined area of the second portion of the outer container having a higher rigidity from the honeycomb sheet than the areas of the outer container other than the predetermined area of the second portion of the outer container and the first portion of the outer container such that the predetermined area is configured to receive the load of the measurement target, and the woven fabrics are stacked on one and another surfaces of the honeycomb sheet; and a superconducting quantum interference device that detects a magnetic field generated from the measurement target, wherein the superconducting quantum interference device is immersed in the refrigerant stored in the accommodation portion of the second tubular container.

* * * * *